(12) United States Patent
Adelman et al.

(10) Patent No.: US 12,344,619 B2
(45) Date of Patent: Jul. 1, 2025

(54) DRUG DELIVERY AND IMAGING CHEMICAL CONJUGATE, FORMULATIONS AND METHODS OF USE THEREOF

(71) Applicant: NANOPHAGIX LLC, Berwyn, PA (US)

(72) Inventors: Steven Jay Adelman, Doylestown, PA (US); H. Donlon Skerrett, Wayne, PA (US); William A. Kinney, Newtown, PA (US)

(73) Assignee: NANOPHAGIX, Berwyn, PA (US)

( * ) Notice: Subject to any disclaimer, the term of this patent is extended or adjusted under 35 U.S.C. 154(b) by 0 days.

(21) Appl. No.: 17/330,417

(22) Filed: May 26, 2021

(65) Prior Publication Data

US 2021/0277016 A1    Sep. 9, 2021

Related U.S. Application Data

(63) Continuation of application No. 15/580,313, filed as application No. PCT/US2016/037580 on Jun. 15, 2016, now Pat. No. 11,034,701.

(60) Provisional application No. 62/180,111, filed on Jun. 16, 2015.

(51) Int. Cl.
| | | |
|---|---|---|
| C07D 491/153 | (2006.01) | |
| A61K 47/54 | (2017.01) | |
| A61P 1/00 | (2006.01) | |
| A61P 9/10 | (2006.01) | |
| A61P 19/02 | (2006.01) | |
| A61P 29/00 | (2006.01) | |
| A61P 35/00 | (2006.01) | |
| C07D 491/18 | (2006.01) | |

(52) U.S. Cl.
CPC ........ *C07D 491/153* (2013.01); *A61K 47/542* (2017.08); *A61P 1/00* (2018.01); *A61P 9/10* (2018.01); *A61P 19/02* (2018.01); *A61P 29/00* (2018.01); *A61P 35/00* (2018.01); *C07D 491/18* (2013.01)

(58) Field of Classification Search
CPC ................................................. C07D 491/153
See application file for complete search history.

(56) References Cited

U.S. PATENT DOCUMENTS

| | | | |
|---|---|---|---|
| 4,160,452 | A | 7/1979 | Theeuwes |
| 4,256,108 | A | 3/1981 | Theeuwes |
| 4,265,874 | A | 5/1981 | Bonsen et al. |
| 4,501,729 | A | 2/1985 | Boucher et al. |
| 5,221,670 | A | 6/1993 | Caufield |
| 5,233,036 | A | 8/1993 | Hughes |
| 5,262,423 | A | 11/1993 | Kao |
| 5,264,610 | A | 11/1993 | Bacon |
| 5,411,967 | A | 5/1995 | Kao et al. |
| 5,718,388 | A | 2/1998 | Czekai et al. |
| 7,560,457 | B2 | 7/2009 | Graziani et al. |
| 8,088,789 | B2 | 1/2012 | Yan et al. |
| 8,158,624 | B2 | 4/2012 | Castanedo et al. |
| 8,221,752 | B2 | 7/2012 | Kasaian et al. |
| 8,236,752 | B1 | 8/2012 | Sung et al. |
| 8,343,955 | B2 | 1/2013 | Blaquiere et al. |
| 8,604,014 | B2 | 12/2013 | Belvin et al. |
| 8,618,107 | B2 | 12/2013 | Barbosa et al. |
| 8,653,089 | B2 | 2/2014 | Heald et al. |
| 8,703,734 | B2 | 4/2014 | Lyakhov et al. |
| 8,748,451 | B2 | 6/2014 | Kozikowski et al. |
| 8,815,926 | B2 | 8/2014 | Furet et al. |
| 8,969,342 | B2 | 3/2015 | Hedstrom et al. |
| 9,024,014 | B2 | 5/2015 | Berstein et al. |
| 9,040,050 | B2 | 5/2015 | Van De Winkel et al. |
| 9,073,927 | B2 | 7/2015 | Pastor Fernandez et al. |
| 9,090,628 | B2 | 7/2015 | Heffron et al. |
| 9,233,998 | B2 | 1/2016 | Anderson et al. |
| 9,249,123 | B2 | 2/2016 | Currie et al. |
| 9,335,320 | B2 | 5/2016 | Ebens, Jr. et al. |
| 9,375,443 | B2 | 6/2016 | Xu et al. |
| 9,434,725 | B2 | 9/2016 | Do et al. |
| 9,474,757 | B2 | 10/2016 | Hege et al. |
| 9,546,182 | B2 | 1/2017 | Dotson et al. |
| 9,650,437 | B2 | 5/2017 | Masternak et al. |
| 9,845,355 | B2 | 12/2017 | Chen et al. |
| 9,856,286 | B2 | 1/2018 | Sheikh et al. |
| 9,943,490 | B2 | 4/2018 | Prud'homme et al. |
| 10,006,091 | B2 | 6/2018 | Gomis et al. |
| 10,195,144 | B2 | 2/2019 | Fahmy et al. |
| 10,231,939 | B2 | 3/2019 | McCord et al. |
| 10,308,634 | B2 | 6/2019 | Bothe et al. |
| 10,450,290 | B2 | 10/2019 | Becker et al. |
| 10,507,315 | B2 | 12/2019 | Hossack et al. |
| 10,526,329 | B2 | 1/2020 | Desroy et al. |
| 10,584,181 | B2 | 3/2020 | Scheer et al. |
| 10,640,516 | B2 | 5/2020 | Cmiljanovic et al. |
| 10,730,862 | B2 | 8/2020 | Crews et al. |
| 2007/0122440 | A1 | 5/2007 | Macosko |
| 2014/0328891 | A1 | 11/2014 | Hunter et al. |
| 2015/0050356 | A1 | 2/2015 | Desai et al. |
| 2015/0290197 | A1 | 10/2015 | Wang et al. |
| 2015/0314016 | A1 | 11/2015 | Chen et al. |
| 2016/0058872 | A1 | 3/2016 | Crew et al. |
| 2016/0213662 | A1 | 7/2016 | Zarnitsyn et al. |
| 2016/0280791 | A1 | 9/2016 | Ghayur et al. |
| 2016/0347816 | A1 | 12/2016 | Toporik et al. |

(Continued)

OTHER PUBLICATIONS

Nicolaou et al. (Chem. Eur. J., 1995, 1(5), pp. 318-333).*

*Primary Examiner* — Susanna Moore
(74) *Attorney, Agent, or Firm* — JUNEAU & MITCHELL; Todd L. Juneau

(57) ABSTRACT

The present invention relates to compounds, and methods of use thereof, capable of entering macrophages. The invention further relates to compounds capable of modulating (for example inhibiting) the activity of the mammalian target of rapamycin (mTor), treating mTor-associated diseases, in particular, but not limited to, related to mTor in macrophages. The invention also relates to compounds capable of imaging mTor in a subject, in particular, but not limited to, mTor in macrophages.

6 Claims, 5 Drawing Sheets

(56) References Cited

U.S. PATENT DOCUMENTS

| | | |
|---|---|---|
| 2017/0283422 A1 | 10/2017 | Gray et al. |
| 2017/0319537 A1 | 11/2017 | Li et al. |
| 2018/0007043 A1 | 1/2018 | Sabourault |
| 2018/0194839 A1 | 7/2018 | Di Padova et al. |
| 2018/0230227 A1 | 8/2018 | Du et al. |
| 2018/0298068 A1 | 10/2018 | Albelda |
| 2018/0369250 A1 | 12/2018 | Elmore et al. |
| 2019/0091194 A1 | 3/2019 | Chin et al. |
| 2019/0167687 A1 | 6/2019 | Chen et al. |

\* cited by examiner

DRUG DELIVERY AND IMAGING CHEMICAL CONJUGATE, FORMULATIONS AND METHODS OF USE THEREOF

BACKGROUND OF THE INVENTION

Macrophages are highly plastic monocyte-derived white blood cells that acquire different molecular and functional phenotypes following exposure to different bioactive molecules and environments. Macrophages can, for example, be dedicated to the removal of foreign materials within body tissues. It has been shown that macrophages have the ability to migrate to areas of inflammation and to deposits of foreign material, such as vascular plaques.

The mechanistic target of rapamycin, also known as the mammalian target of rapamycin (mTor), is an evolutionarily conserved ser/thr protein kinase that controls many critical cellular processes including growth, protein translation, metabolic flux, and cell survival. mTor functions as the core catalytic component of two structurally and functionally distinct signaling complexes. mTor complex 1 (mTorC1) regulates cell growth and is responsible for the well-characterized role of mTOR in controlling protein translation whereas mTor complex 2 (mTorC2) regulates cell survival and the actin cytoskeleton.

There remains a need in the art for the ability to deliver compounds specifically to macrophages, which is important for the treatment of various diseases and disorders, including inflammatory diseases, immune diseases, and any diseases or disorders related to macrophages. There also remains a need in the art for inhibitors and modulators of mTor, in particular inhibitors and modulators of mTor having an ability to enter macrophages and modulate macrophage-related diseases and disorders. There also remains a need in the art for compounds with an ability to enter macrophages and act as imaging agents. There also remains a need in the art for inhibitors and modulators of mTor, in particular inhibitors and modulators of mTor having an ability to enter macrophages and modulate macrophage-related diseases and disorders, and at the same time having the ability to act as imaging agents. The present invention fulfills these needs.

SUMMARY OF THE INVENTION

In one aspect, the invention relates to a compound of Formula 1:

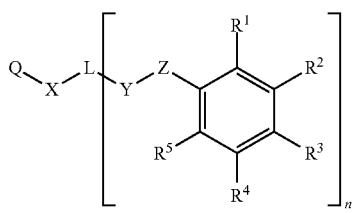

Formula 1 wherein in Formula 1,
X is selected from the group consisting of carbonyl, and a bond;
Y and Z are each independently selected from the group consisting of null, bond, oxygen, carbonyl, and amine;
L is selected from the group consisting of null and a linker, wherein when L is a linker, it comprises at least one selected from the group consisting of a bond, a normal alkyl, a branched alkyl, an aryl, an ester, an ether, and an amide;

$R^1$, $R^2$, $R^3$, $R^4$, and $R^5$ are each independently selected from the group consisting of H, F, Cl, Br, I, $NR^6R^7$, $NR^6C(=O)R^7$, $C_{1-6}$ alkyl, $C_{1-6}$ haloalkyl, $C_{2-6}$ alkenyl, $C_{2-6}$ alkynyl, wherein $R^6$ and $R^7$ are selected from the group consisting of H, and optionally substituted $C_{1-6}$ alkyl, $C_{1-6}$ haloalkyl, $C_{2-6}$ alkenyl, $C_{2-6}$ alkynyl;

n is 1 or 2; and

Q is selected from the group consisting of:

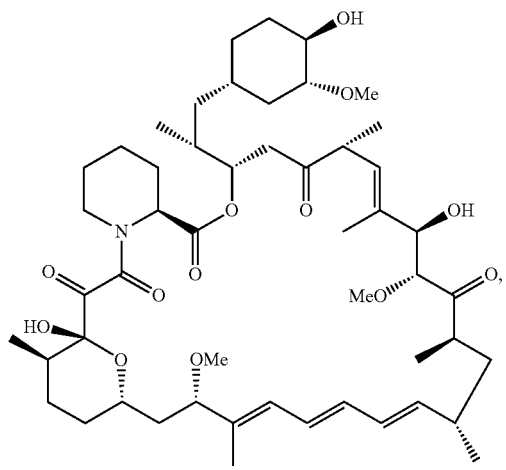

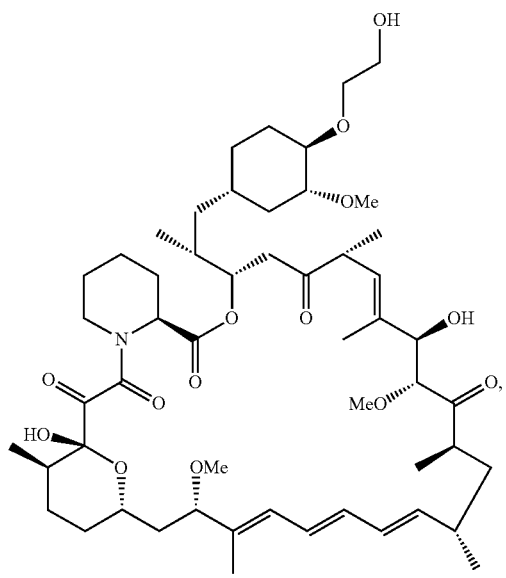

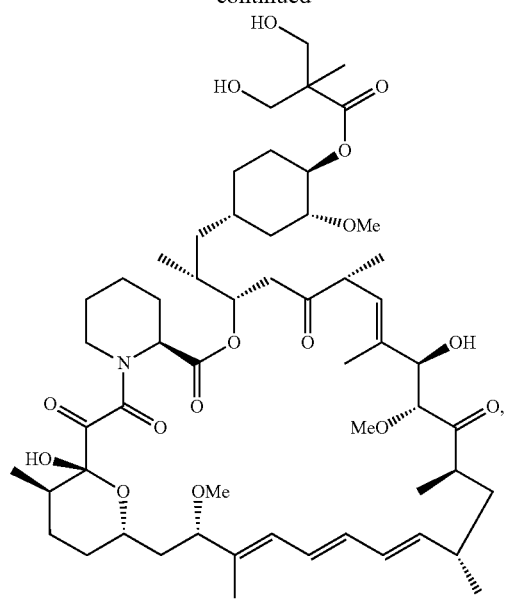
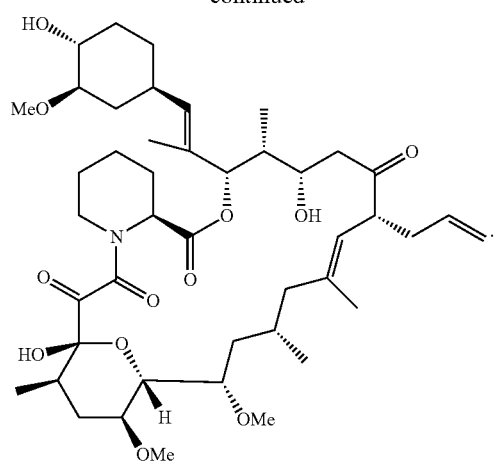
In one embodiment, Q is selected from the group consisting of:
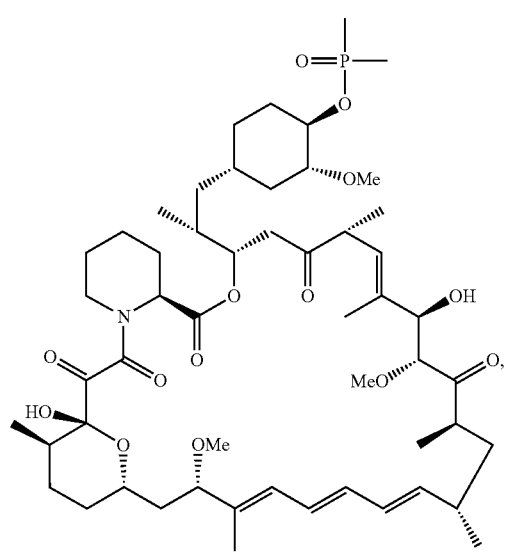
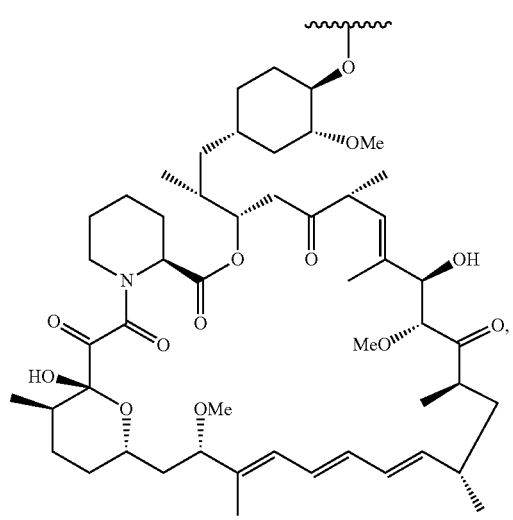
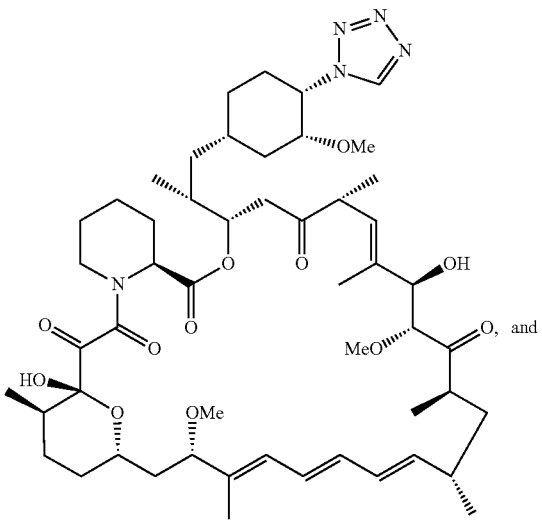
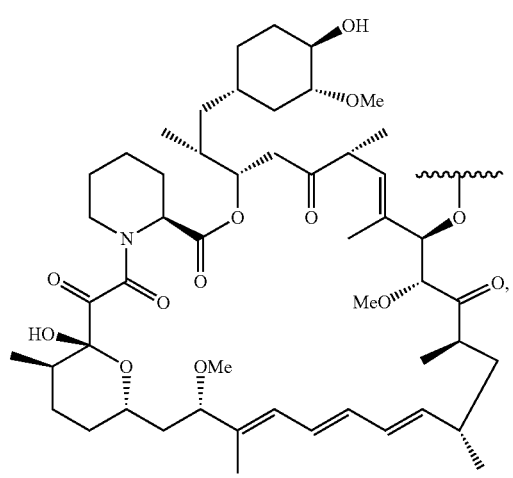

5
-continued
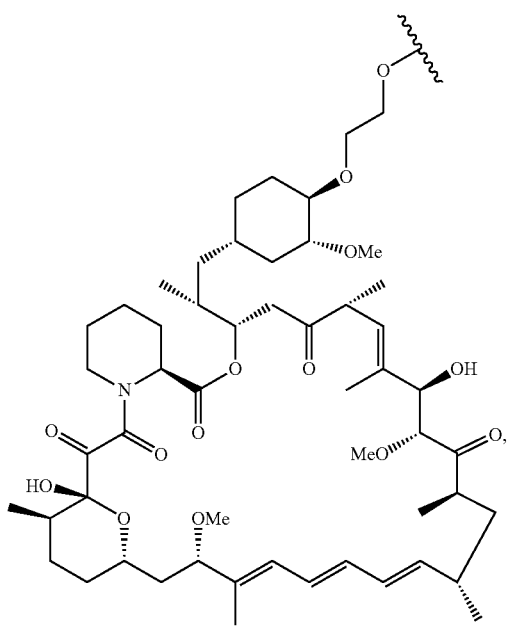
6
-continued
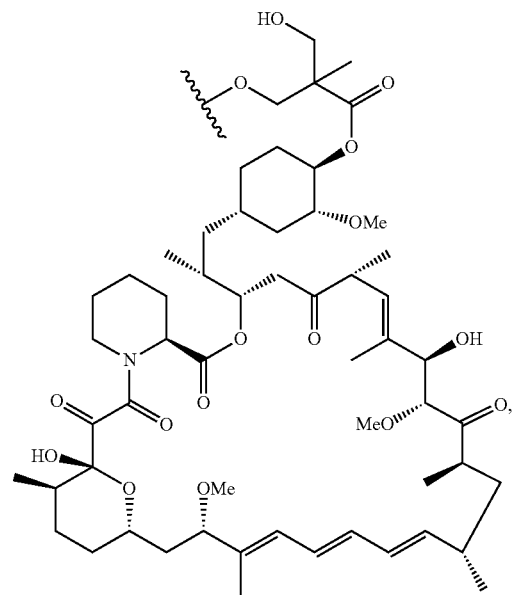
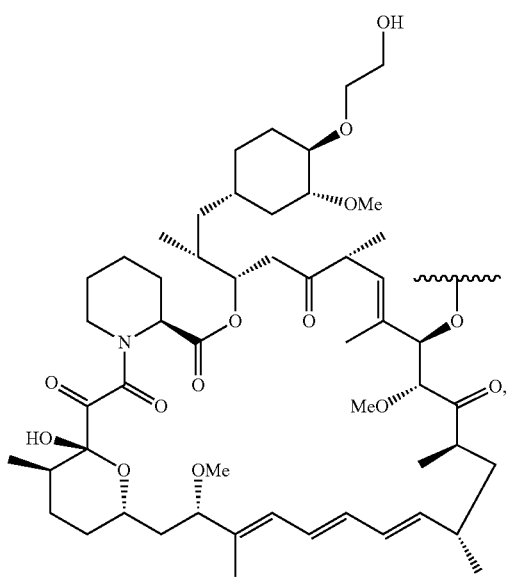
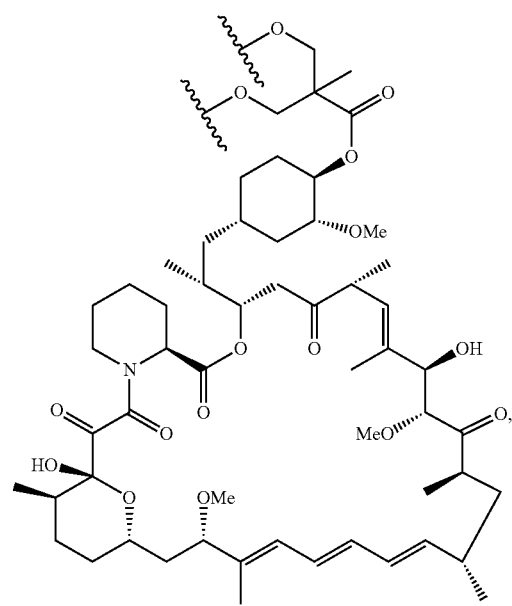

-continued

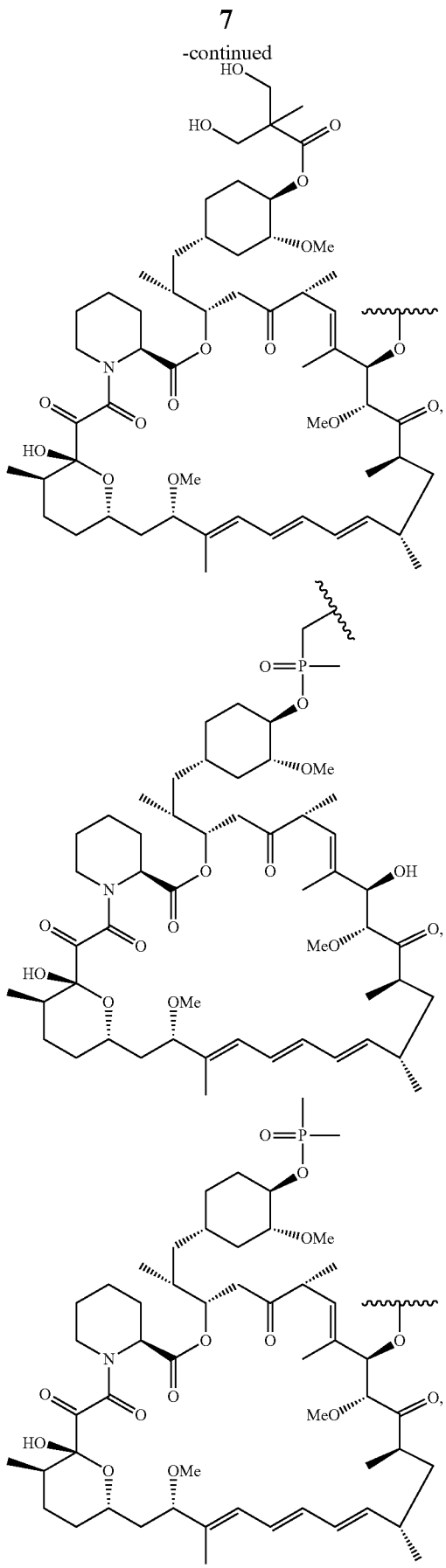

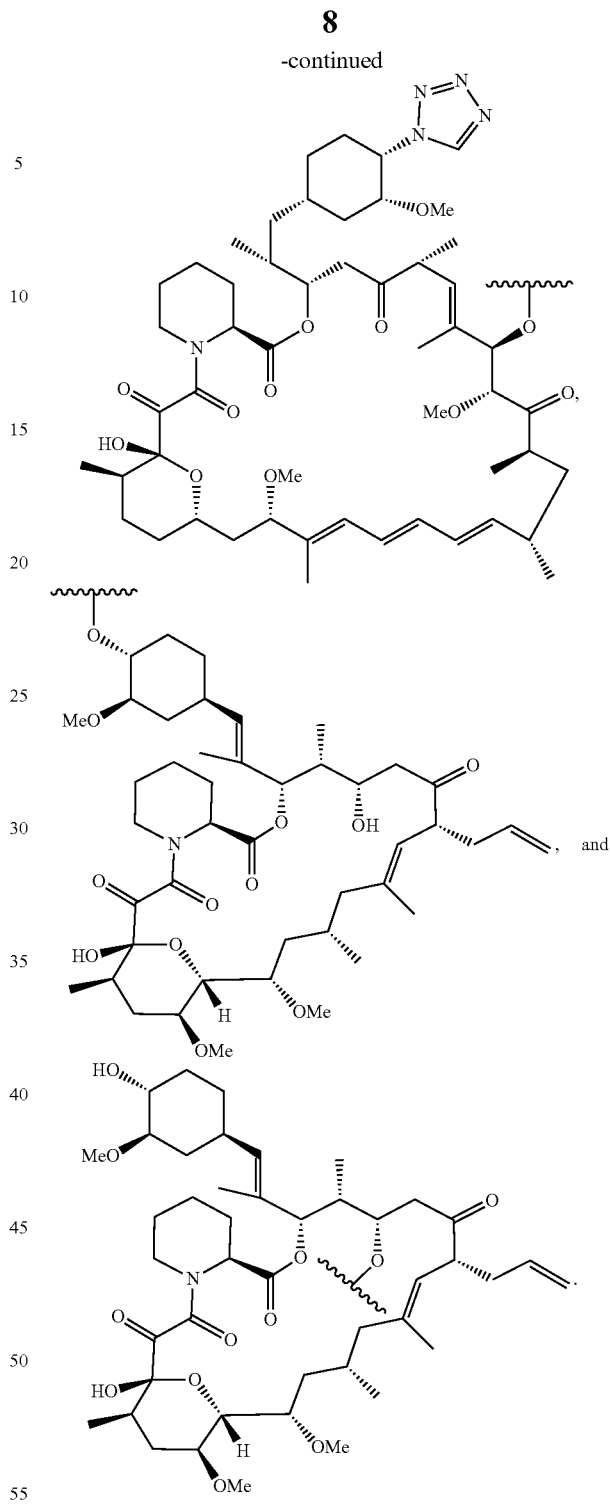

In another embodiment, $R^1$, $R^2$, $R^3$, $R^4$, and $R^5$ are each independently selected from the group consisting of H, I, $NR^6C(=O)R^7$, and $C_{1-6}$ alkyl, wherein $R^6$ and $R^7$ are selected from the group consisting of H, and optionally substituted $C_{1-6}$ alkyl. In another embodiment, $R^1$, $R^3$, and $R^5$ are each I, and $R^2$ and $R^4$ are each $NHC(=O)CH_3$. In another embodiment, L is a $C_{1-12}$ straight or branched alkyl optionally substituted with hydroxyl groups.

In one embodiment, the compound is selected from the group consisting of:

9
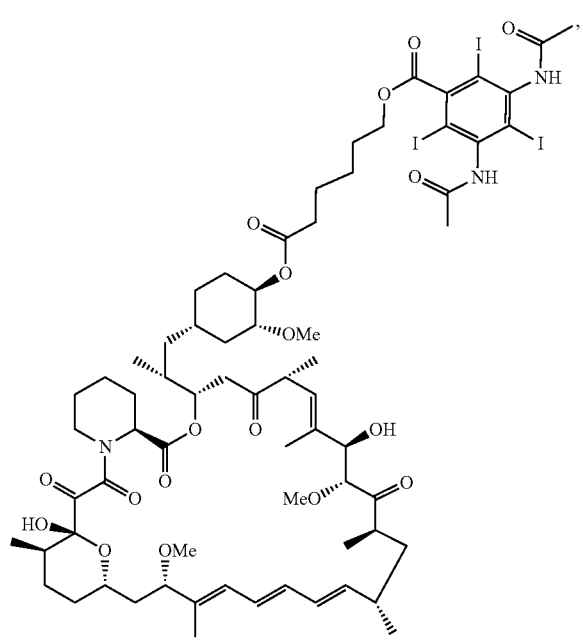
10
-continued
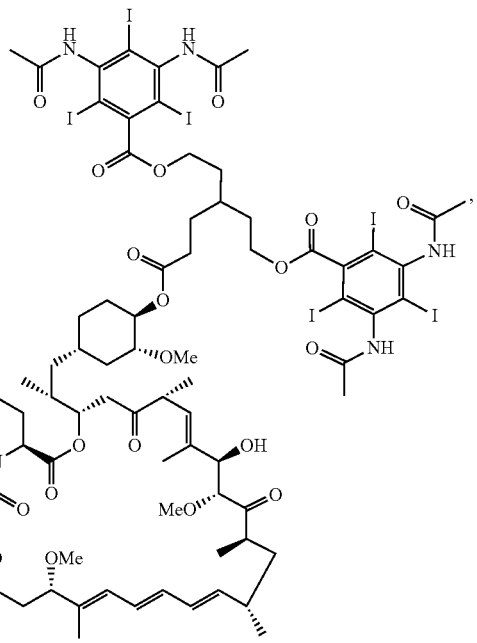
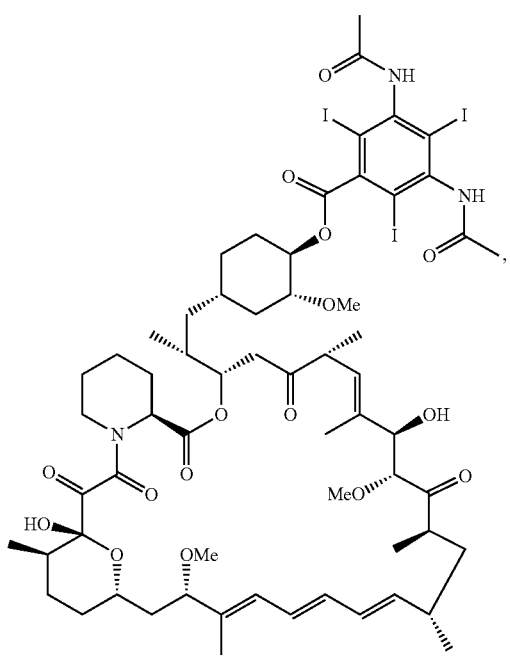
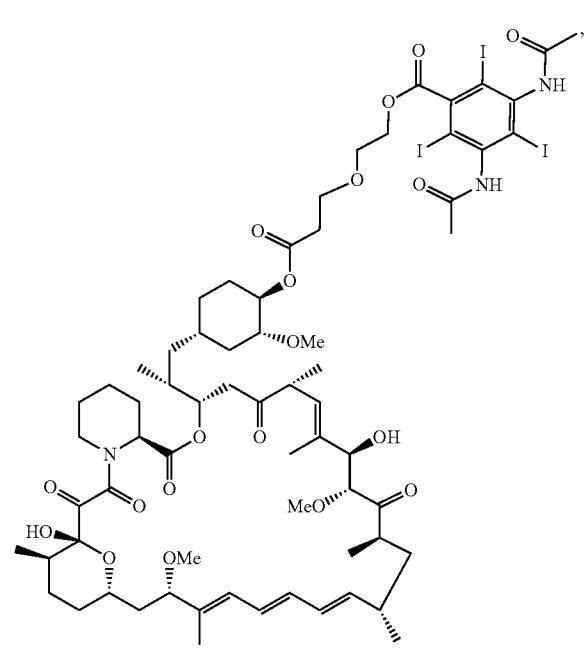

11
-continued
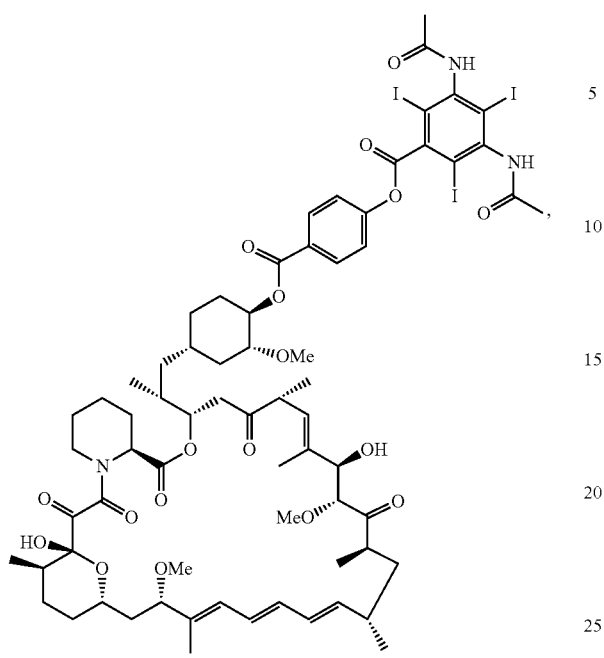
12
-continued
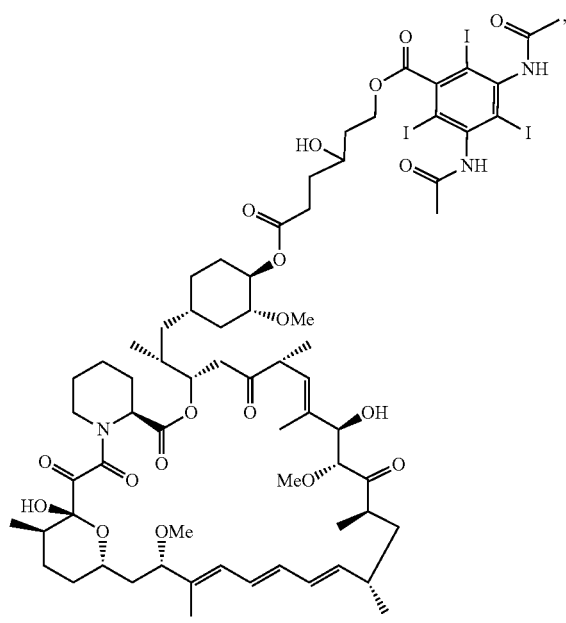
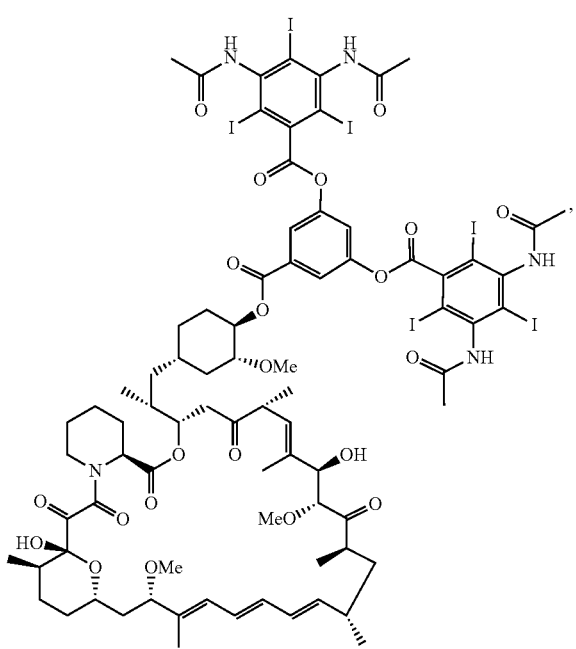

13
-continued
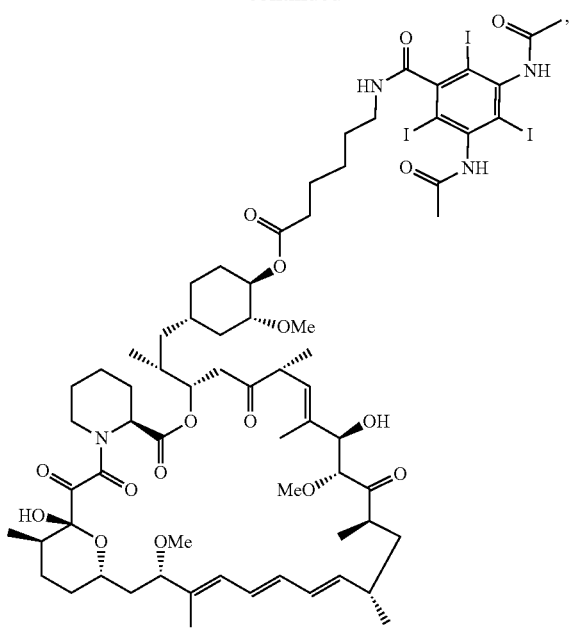
and
14
-continued
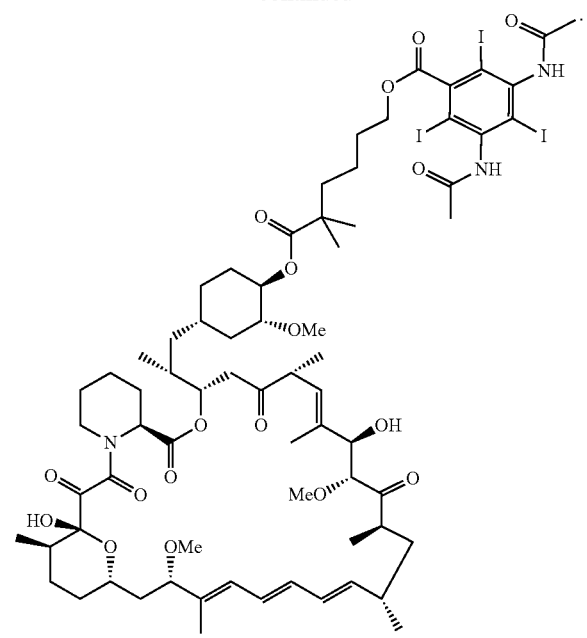
In one embodiment, the compound of is represented by Formula 2:
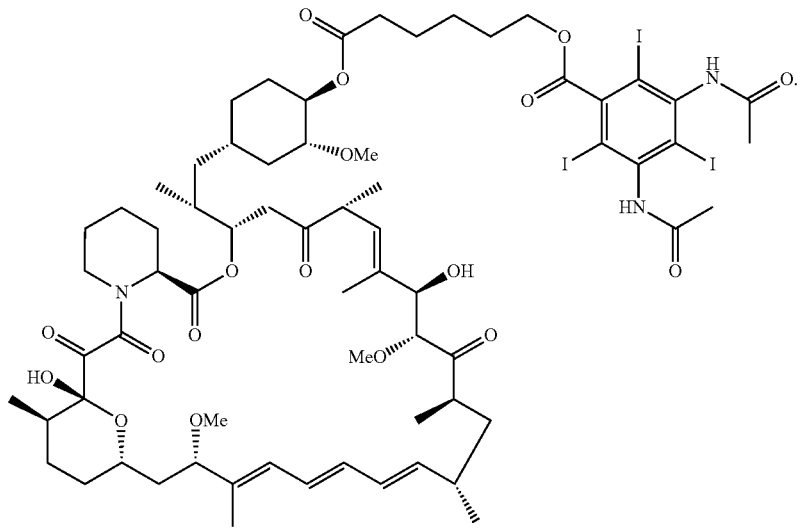
Formula 2

In another aspect, the invention relates to a composition comprising a compound of Formula 1, and a pharmaceutically acceptable carrier. In one embodiment, the compound is formulated into particles. In one embodiment, the size of the particles ranges from 2000 nm to 5 nm. In another embodiment, the size of the particles ranges from 200 nm to 5 nm. In another embodiment, the size of the particles ranges from 140 nm to 80 nm. In one embodiment, the compound is represented by Formula 2.

In one aspect, the invention relates to a method of treating or preventing a disease or disorder in a subject in need thereof, comprising the step of administering to the subject a therapeutically effective amount of the compound of Formula 1. In one embodiment, the disease or disorder is at least one selected from the group consisting of atherosclerosis, sarcoidosis, an inflammatory disease, chronic obstructive pulmonary disease (COPD), emphysema, heart failure, vasculitis, rheumatoid arthritis, osteoarthritis, peripheral artery disease (PAD), sepsis, sepsis in late-stage cancer patients, ischemia, phlebitis, colitis, celiac disease, chronic inflammatory bowel disease, Crohn's disease, chronic prostatitis, interstitial cystitis, angiogenesis associated with tumor formation, cervical cancer, cardiomyopathy, and rhinitis. In another embodiment, the disease or condition is associated with the mammalian target of rapamycin (mTor). In another embodiment, the compound is represented by Formula 2.

In another aspect, the invention relates to a method of imaging mTor in a subject, comprising the step of administering to the subject an effective amount of the compound of Formula 1. In one embodiment, the compound is represented by Formula 2.

In another aspect, the invention relates to a method of treating or preventing a disease or disorder in a subject in need thereof, and of imaging mTor in a subject, comprising the step of administering to the subject a therapeutically effective amount of the compound of Formula 1. In one embodiment, the compound is represented by Formula 2.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
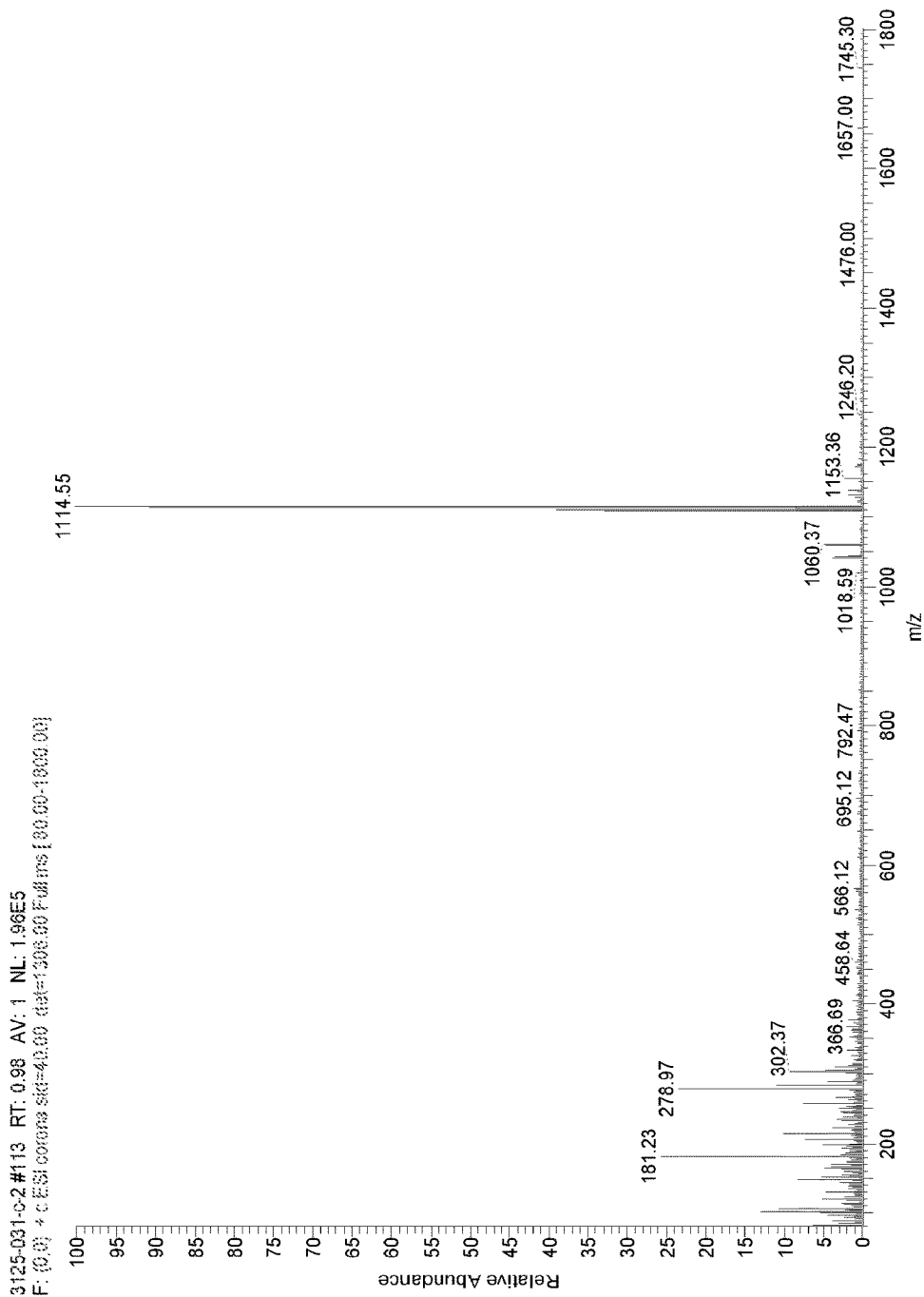
FIG. 1 depicts a mass spectrum of intermediate A.

The present invention provides novel chemical entities, and compositions and formulations thereof, capable of entering macrophages. The compounds of the invention, and the compositions and formulations thereof, are also useful for modulating the activity of mTor, in particular modulating the activity of mTor inside a macrophage. The compounds of the invention, and the compositions and formulations thereof, are potential therapeutics for various diseases and disorders, including but not limited to, atherosclerosis, sarcoidosis, diseases in which inflammation occurs in the lymph nodes, lungs, liver, eyes, skin, or other tissues, chronic obstructive pulmonary disease (COPD), emphysema, heart failure, vasculitis, rheumatoid arthritis, osteoarthritis, peripheral artery disease (PAD), sepsis, sepsis in late-stage cancer patients, ischemia, phlebitis, colitis, celiac disease, chronic inflammatory bowel disease, Crohn's disease, chronic prostatitis, interstitial cystitis, angiogenesis associated with tumor formation, cervical cancer, cardiomyopathy, and rhinitis. The compounds of the invention, and the compositions and formulations thereof, are also capable of acting as imaging agents, particularly as imaging agents for macrophage related diseases. The compounds of the invention, and the compositions and formulations thereof, are also capable of acting as both imaging agents, and therapeutic agents, particularly as imaging and therapeutic agents for macrophage related diseases.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e., to at least one) of the grammatical object of the article. By way of example, "an element" means one element or more than one element.

The term "about" as used herein when referring to a measurable value such as an amount, a temporal duration, and the like, is meant to encompass variations of ±20% or ±10%, more preferably ±5%, even more preferably ±1%, and still more preferably ±0.10%

The terms "patient," "subject," "individual," and the like are used interchangeably herein, and refer to any animal, including mammals. In certain non-limiting embodiments, the patient, subject or individual is a human.

A "disease" is a state of health of an a subject wherein the subject cannot maintain homeostasis, and wherein if the disease is not ameliorated, the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, "treating a disease or disorder" means reducing the frequency and/or severity with which a sign or symptom of the disease or disorder is experienced by an individual.

The term "treat," as used herein, means reducing the frequency and/or severity of a sign or symptom of a disease or disorder experienced by a subject. Thus, "treat" and "treating" are not limited to the case where the subject (e.g., patient) is cured and the disease or disorder is eradicated. Rather, the present invention also contemplates treatment that merely reduces a sign or symptom, improves (to some degree) and/or delays disease or disorder progression. The term "treatment" also refers to the alleviation, amelioration, and/or stabilization of signs or symptoms, as well as a delay in the progression of signs or symptoms of a disease or disorder.

As used herein, to "alleviate" a disease or disorder means to reduce the frequency and/or severity of one or more signs and/or symptoms of the disease or disorder experienced by the subject The term "effective amount", as used herein, refers to an amount that provides a therapeutic or prophylactic benefit in the subject.

The term "therapeutically effective amount" refers to the amount of the compound that will elicit a biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the signs and/or symptoms of the disease or disorder being treated. The therapeutically effective amount will vary depending on the compound, the disease or disorder, the severity of the disease or disorder, and the age, weight, etc., of the subject to be treated.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "composition" refers to a mixture of at least one compound or molecule useful within the invention with one or more different compound, molecule, or material.

As used herein "pharmaceutical composition" or "pharmaceutically acceptable composition" refers to specific examples of compositions, wherein at least one compound or molecule useful within the invention is mixed with one or more pharmaceutically acceptable carriers. In some instances, the pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the terms "bioconjugation," "conjugation," and/or "conjugate(s)," unless otherwise stated, refer to the chemical derivatization of a preexisting molecule with another molecular entity. The molecular entity can be any molecule and can include a small molecule or a macromolecule. Examples of molecular entities include, but are not limited to, compounds of the invention, macromolecules, polymers or resins, such as polyethylene glycol (PEG) or polystyrene, non-immunogenic high molecular weight compounds, fluorescent, chemiluminescent radioisotope and bioluminescent marker compounds, antibodies, biotin, diagnostic detector molecules, such as a maleimide derivatized fluorescein, coumarin, a metal chelator or any other modifying group. The terms bioconjugation and conjugation are used interchangeably throughout the Specification.

As used herein, the terms "imaging agent," "imaging probe," or "imaging compound," means, unless otherwise stated, a molecule which can be detected by its emitted signal, such as positron emission, autofluorescence emission, or optical properties, or a radio-opaque molecule. The method of detection of the compounds may include, but are not necessarily limited to, nuclear scintigraphy, positron emission tomography (PET), single photon emission computed tomography (SPECT), magnetic resonance imaging, magnetic resonance spectroscopy, computed tomography, X-ray, or a combination thereof depending on the intended use and the imaging methodology available to the medical or research personnel.

As used herein, the term "substituted" means that an atom or group of atoms has replaced hydrogen as the substituent attached to another group. The term "substituted" further refers to any level of substitution, namely mono-, di-, tri-, tetra-, or pentasubstitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, the term "alkyl," by itself or as part of another substituent means, unless otherwise stated, a straight or branched chain hydrocarbon having the number of carbon atoms designated (i.e. C$_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is (C$_1$-C$_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range and, when appropriate, partial integers of the numerical values within ranges. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds of the Invention

In one aspect, the invention relates to a compound of Formula 1:

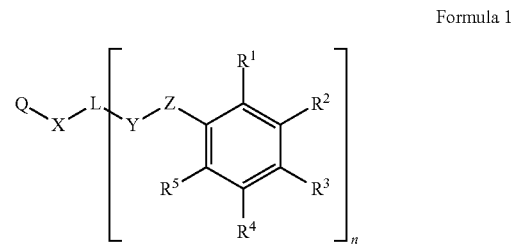

Formula 1 wherein in Formula 1,

X is selected from the group consisting of carbonyl, and a bond;

Y and Z are each independently selected from the group consisting of null, bond, oxygen, carbonyl, and amine;

L is selected from the group consisting of null and a linker, wherein when L is a linker, it comprises at least one selected from the group consisting of a bond, a normal alkyl, a branched alkyl, an optionally substituted alkyl, an aryl, an optionally substituted aryl, an ester, an ether, and an amide;

R$^1$, R$^2$, R$^3$, R$^4$, and R$^5$ are each independently selected from the group consisting of H, F, Cl, Br, I, NR$^6$R$^7$, NR$^6$C(=O)R$^7$, C$_{1-6}$ alkyl, C$_{1-6}$ haloalkyl, C$_{2-6}$ alkenyl, C$_{2-6}$ alkynyl, wherein R$^6$ and R$^7$ are selected from the group consisting of H, and optionally substituted C$_{1-6}$ alkyl, C$_{1-6}$ haloalkyl, C$_{2-6}$ alkenyl, C$_{2-6}$ alkynyl;

n is 1 or 2; and

Q is selected from the group consisting of:

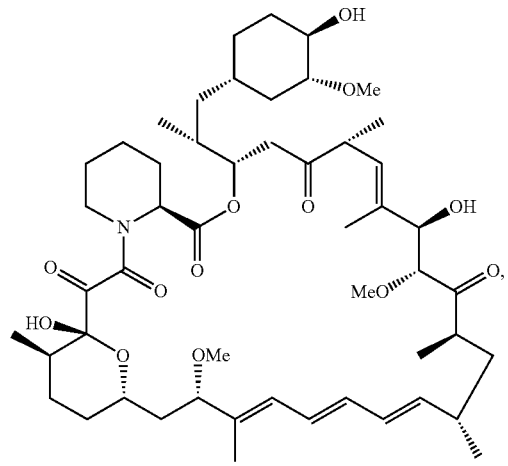

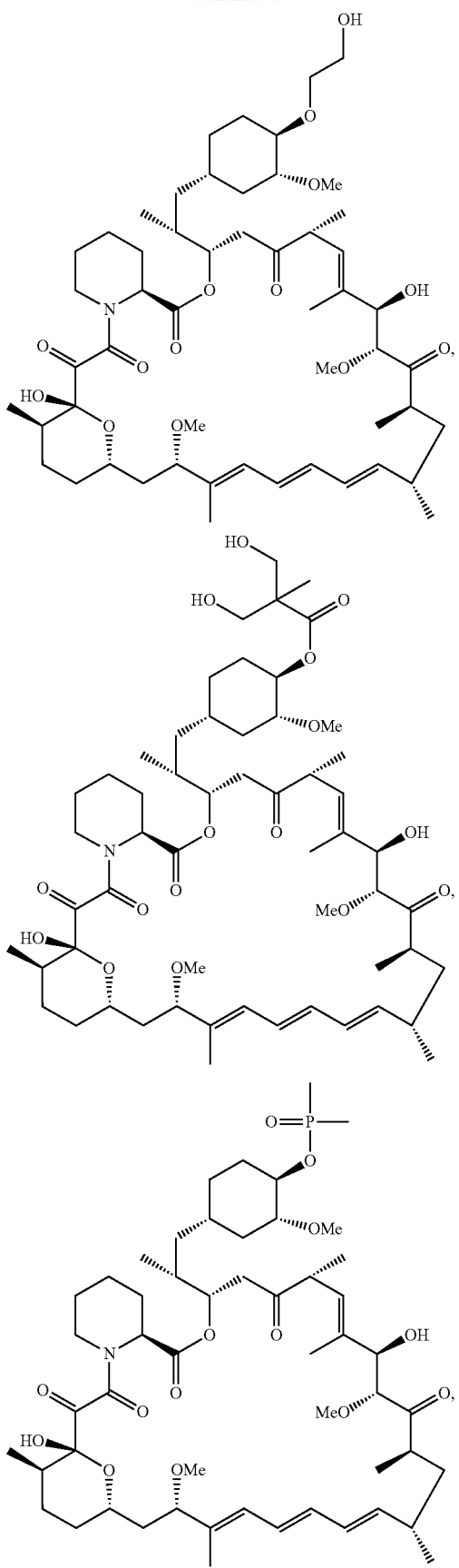

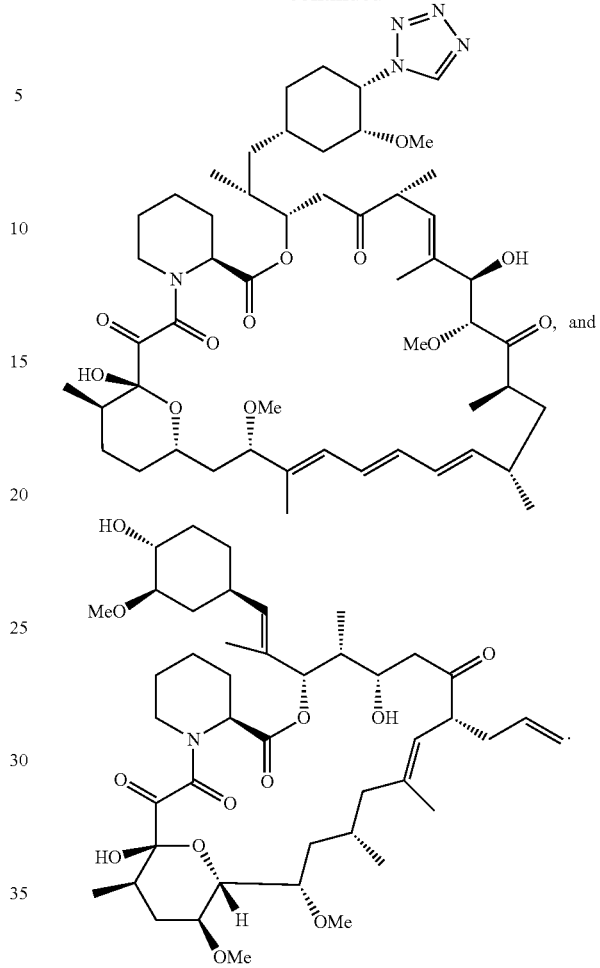

In one embodiment, the point of attachment between Q and X is one or more carbon or oxygen atoms of Q.

In some embodiments, at least one of $R^1$, $R^2$, $R^3$, $R^4$, and $R^5$ is not H. In some embodiments, neither of $R^1$, $R^2$, $R^3$, $R^4$, or $R^5$ is H. In other embodiments, neither of $R^1$, $R^2$, $R^3$, $R^4$, or $R^5$ is a methyl group. In other embodiments, neither of $R^1$, $R^2$, $R^3$, $R^4$, or $R^5$ is an acyl group substituent, a carboxyl substituent, or an alkylated carboxyl substituent. In some embodiments, only one of $R^1$, $R^2$, $R^3$, $R^4$, and $R^5$ can be fluorine. In some embodiments, at least four of $R^1$, $R^2$, $R^3$, $R^4$, and $R^5$ are not a fluorine. In other embodiments, neither of $R^1$, $R^2$, $R^3$, $R^4$, or $R^5$ is a fluorine. In some embodiments, at least three of $R^1$, $R^2$, $R^3$, $R^4$, or $R^5$ connect with another one of $R^1$, $R^2$, $R^3$, $R^4$, or $R^5$ to form a cycle. In other embodiments, neither of $R^1$, $R^2$, $R^3$, $R^4$, or $R^5$ connects with another one of $R^1$, $R^2$, $R^3$, $R^4$, or $R^5$ to form a cycle. In some embodiments, at least one of $R^1$, $R^2$, $R^3$, $R^4$, and $R^5$ is iodine. In other embodiments, at least two of $R^1$, $R^2$, $R^3$, $R^4$, and $R^5$ are iodine. In other embodiments, at least three of $R^1$, $R^2$, $R^3$, $R^4$, and $R^5$ are iodine. In some embodiments, at least one of $R^1$, $R^2$, $R^3$, $R^4$, and $R^5$ is $NR^6C(=O)R^7$, wherein $R^6$ and $R^7$ are selected from the group consisting of H, and optionally substituted $C_{1-6}$ alkyl. In some embodiments, at least two of $R^1$, $R^2$, $R^3$, $R^4$, and $R^5$ are $NR^6C(=O)R^7$, wherein $R^6$ and $R^7$ are selected from the group consisting of H, and optionally substituted $C_{1-6}$ alkyl.

In one embodiment, Q is selected from the group consisting of.

23
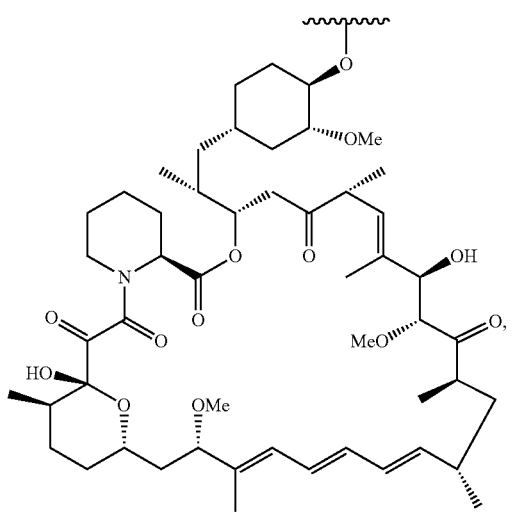
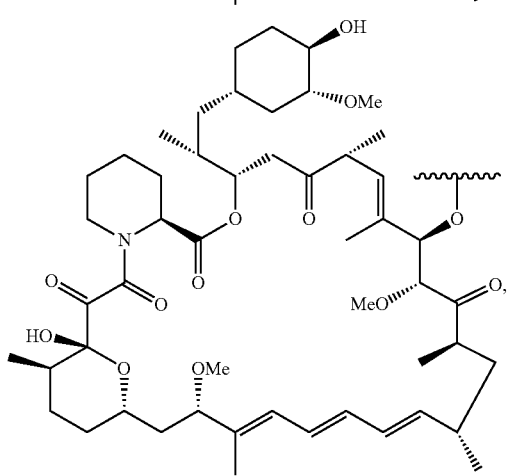
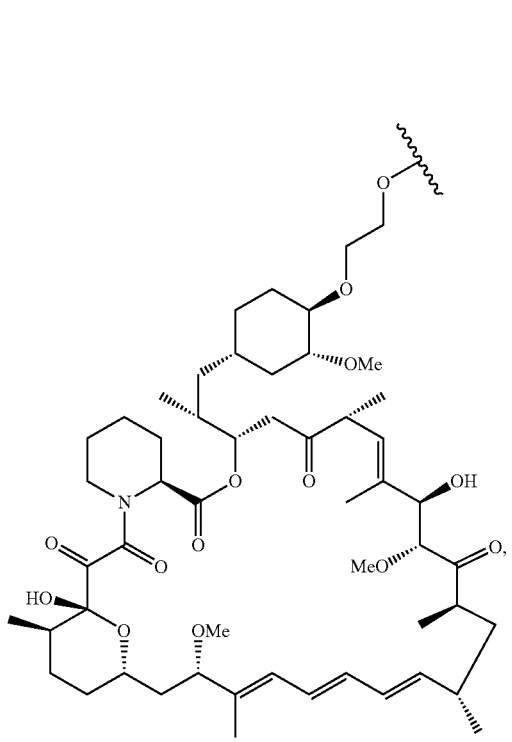
24
-continued
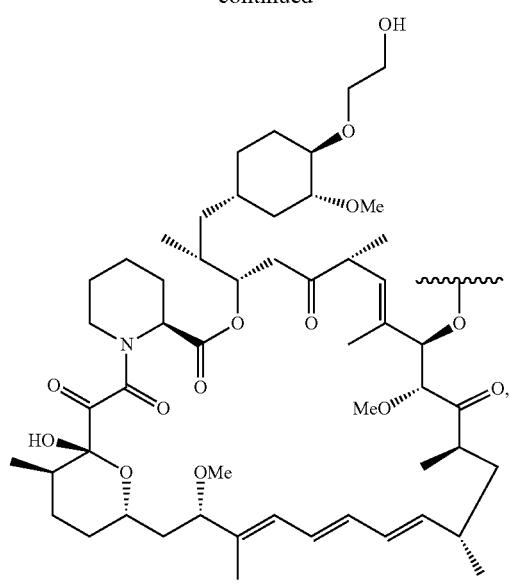
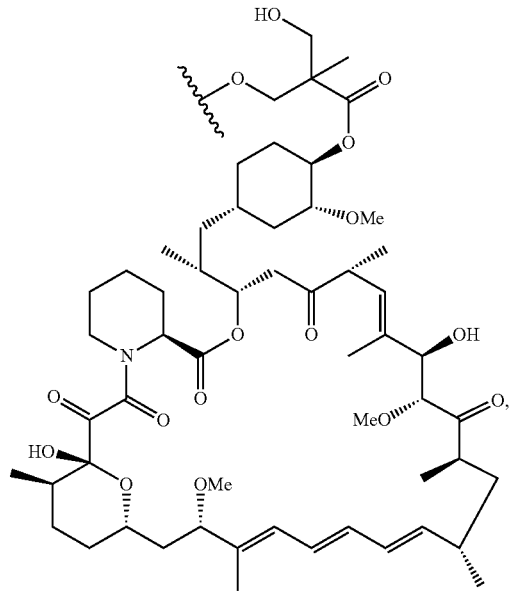

25
-continued
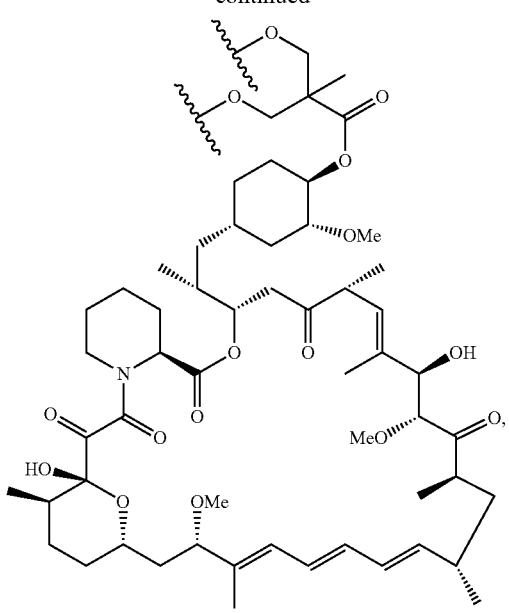
26
-continued
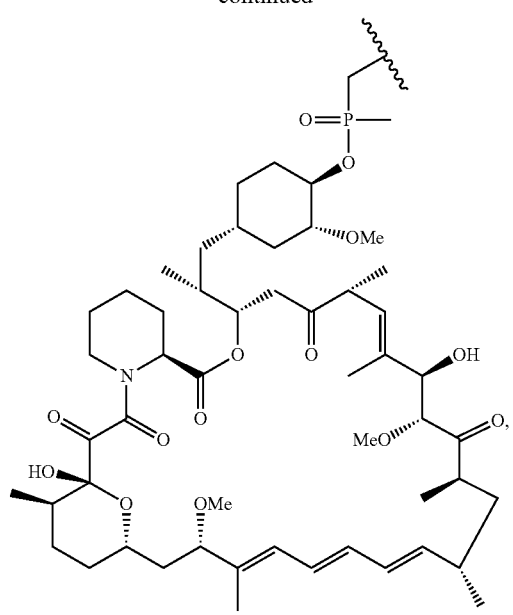
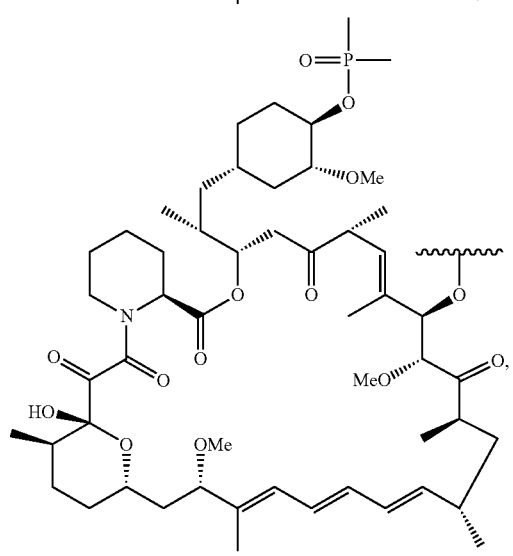
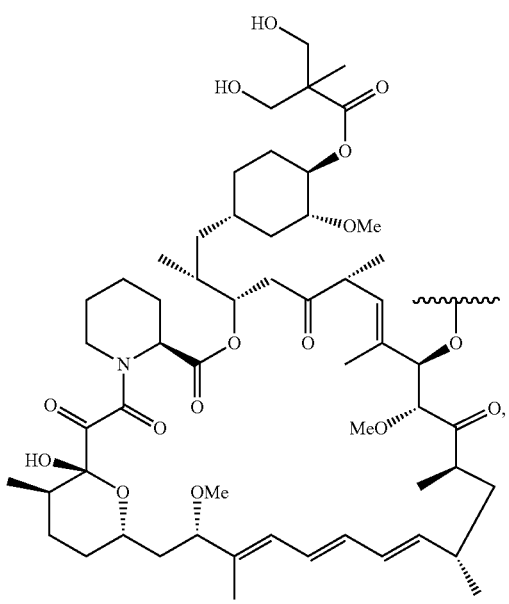
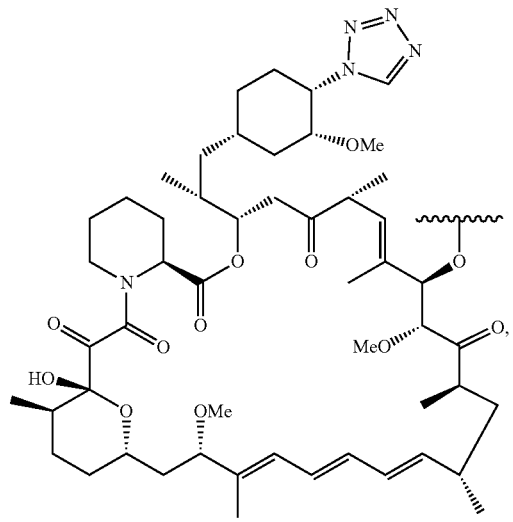

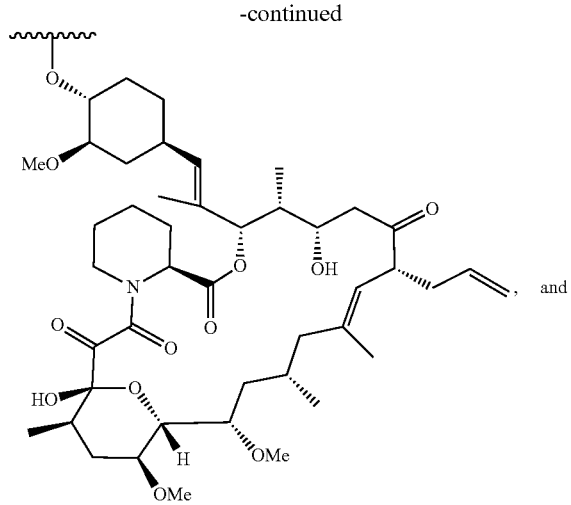

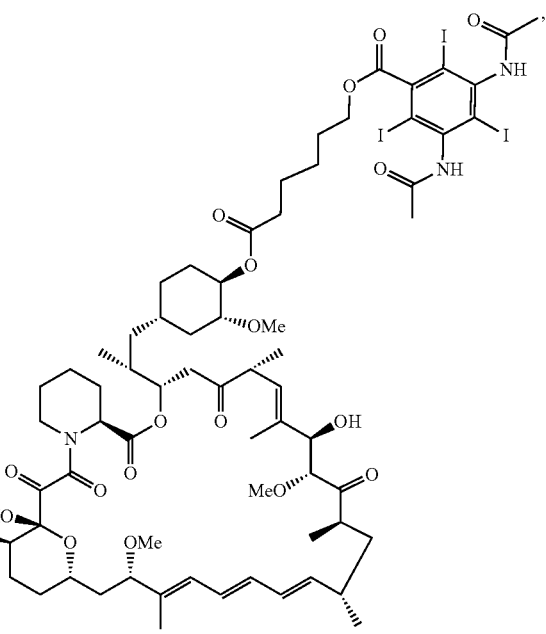

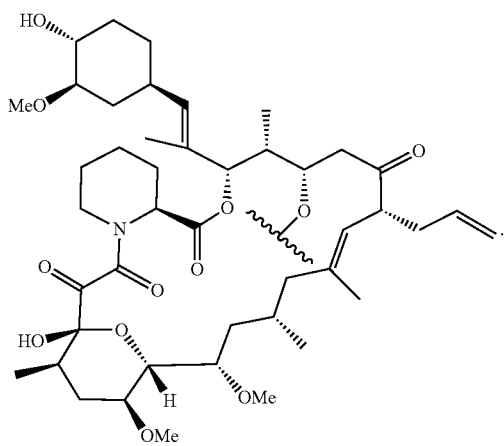

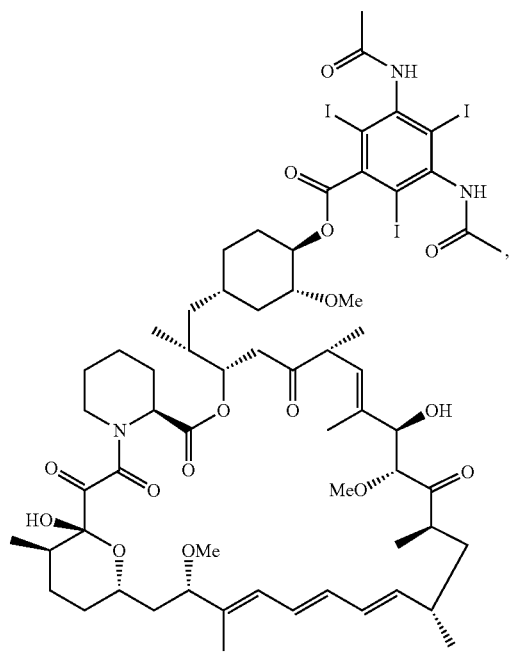

In one embodiment, $R^1$, $R^2$, $R^3$, $R^4$, and $R^5$ are each independently selected from the group consisting of H, I, $NR^6C(=O)R^7$, and $C_{1-6}$ alkyl, wherein $R^6$ and $R^7$ are selected from the group consisting of H, and optionally substituted $C_{1-6}$ alkyl. In another embodiment, $R^1$, $R^3$, and $R^5$ are each I, and $R^2$ and $R^4$ are each $NHC(=O)CH_3$. In another embodiment, L is a $C_{1-12}$ straight or branched alkyl optionally substituted with hydroxyl groups.

In one embodiment, the compound is selected from the group consisting of:

29
-continued
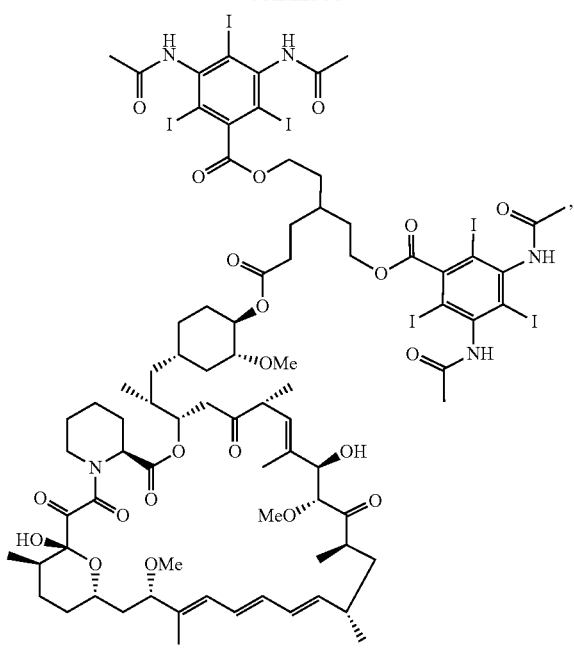
30
-continued
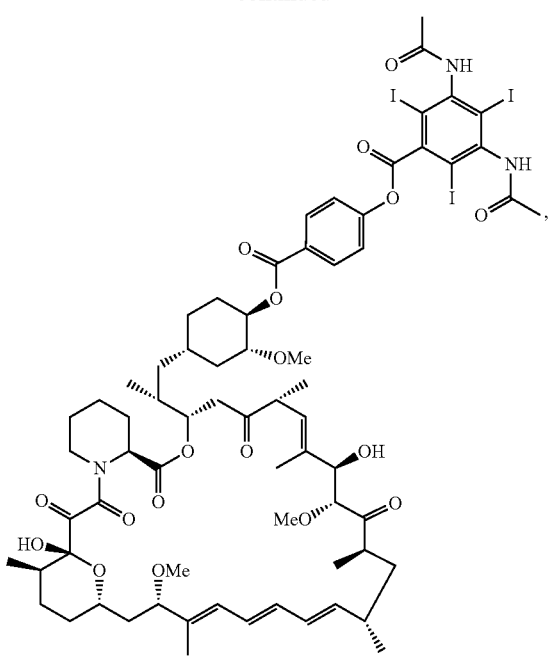
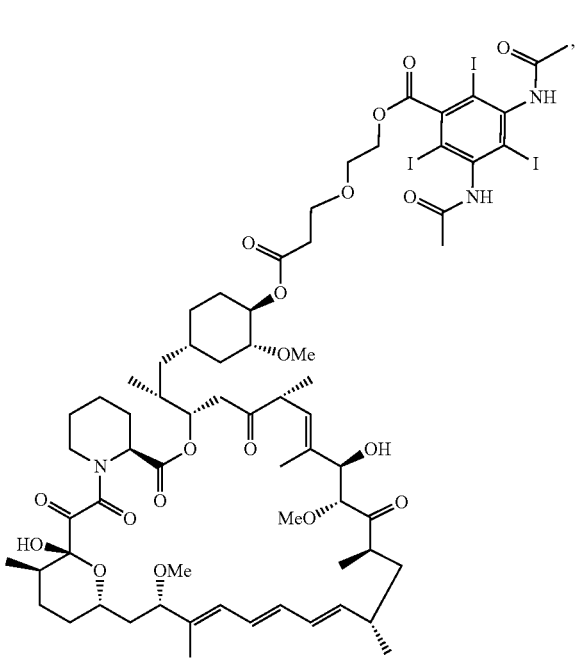

31
-continued
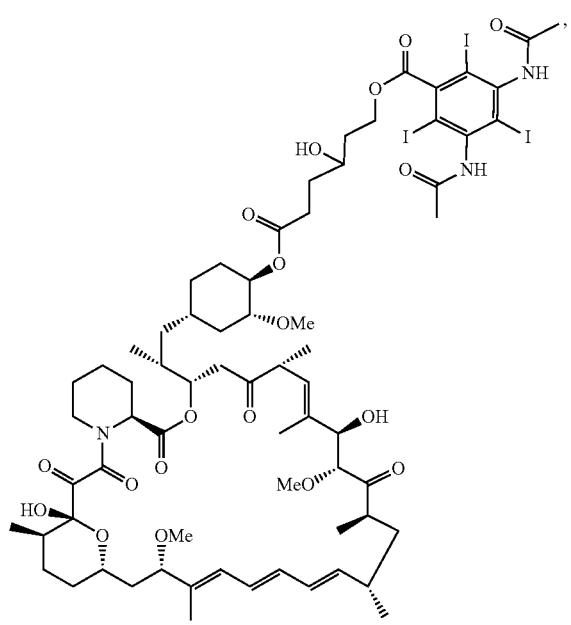
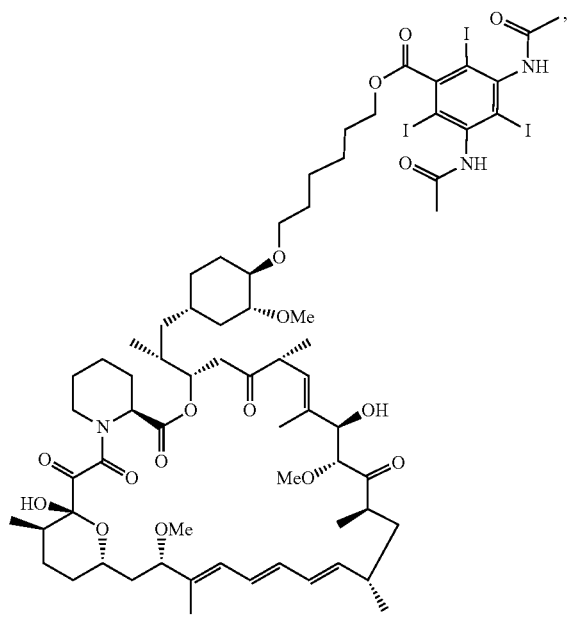
32
-continued
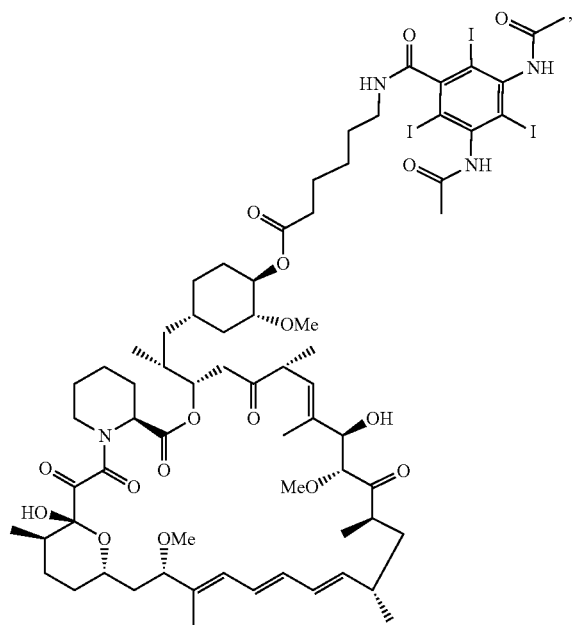
and
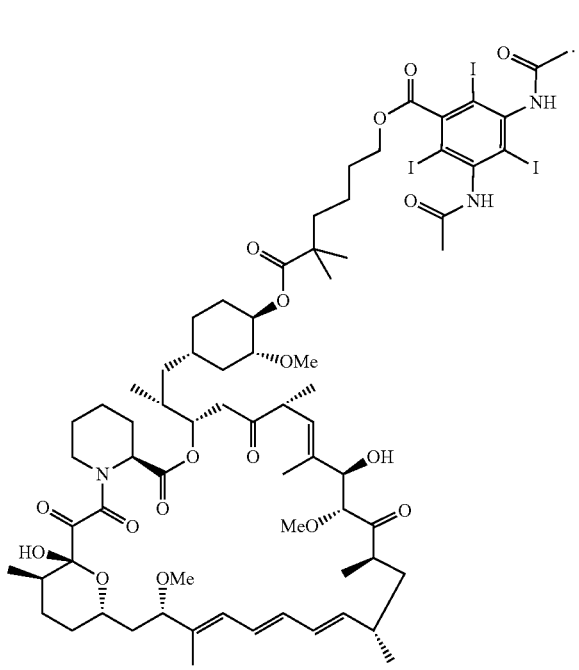
In another embodiment, the compound is represented by Formula 2:

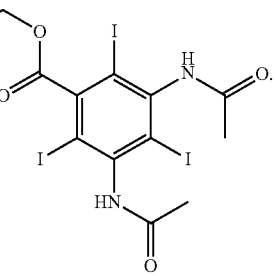

Formula 2

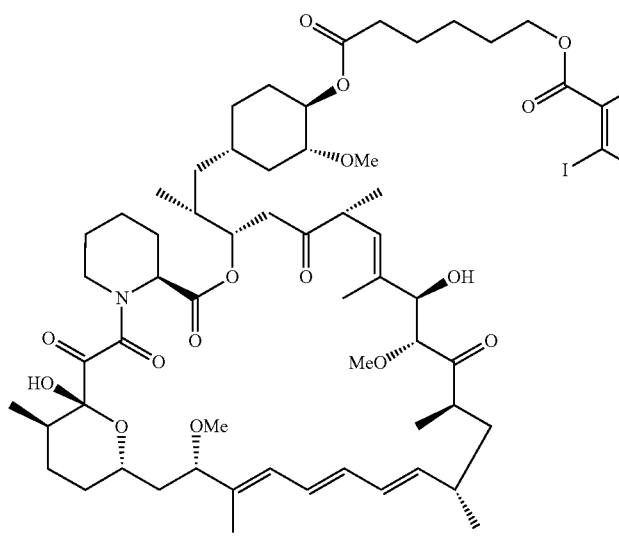

Formulations of the Invention

In one aspect, the compounds of the invention are part of certain formulations. In some embodiments, the formulations comprise the compound of the invention milled to within certain particle sizes distribution, such as for example described in U.S. Pat. Nos. 5,862,999 and 5,718,388, descriptions incorporated herein in their entirety. In other embodiments, the compound is formulated into nanoparticles using any method known in the art, such as for example described in U.S. Pat. App. No. 2004/0076586, description incorporated herein in its entirety. In another embodiment, the compound is formulated into nanoparticles by flash nanoprecipitation, such as for example described in U.S. Pat. App. Nos. 2010/0330368 and 2007/0122440, and Gindy et al., 2009, Expert Opinion on Drug Delivery, 6(8):865-878, descriptions incorporated herein in their entirety. In another embodiment, the compound is formulated by cavitation, such as for example described in U.S. Pat. App. No. 2013/0203717, description incorporated herein in its entirety. In another embodiment, the compound is formulated into nanocrystals, such as for example described in Junghanns et al., 2008, Int J Nanomedicine, 3(3):295-310, description incorporated herein in its entirety.

In another aspect, the compounds of the invention are formulated as particles. In one embodiment, the particles are nanocrystals. In one embodiment, the particles are obtained by milling. In one embodiment, the particles are obtained by nanoprecipitation. In one embodiment, the particle size ranges from about 2000 nm to about 200 nm. In one embodiment, the particle size ranges from about 140 nm to about 80 nm. In one embodiment, the particles size ranges from about 190 nm to about 5 nm.

In one embodiment, the average size of the particles is less than about 2000 nm. In one embodiment, the average size of the particles is less than about 1900 nm. In one embodiment, the average size of the particles is less than about 1800 nm. In one embodiment, the average size of the particles is less than about 1700 nm. In one embodiment, the average size of the particles is less than about 1600 nm. In one embodiment, the average size of the particles is less than about 1500 nm. In one embodiment, the average size of the particles is less than about 1400 nm. In one embodiment, the average size of the particles is less than about 1300 nm. In one embodiment, the average size of the particles is less than about 1200 nm. In one embodiment, the average size of the particles is less than about 1100 nm. In one embodiment, the average size of the particles is less than about 1000 nm. In one embodiment, the average size of the particles is less than about 900 nm. In one embodiment, the average size of the particles is less than about 800 nm. In one embodiment, the average size of the particles is less than about 700 nm. In one embodiment, the average size of the particles is less than about 600 nm. In one embodiment, the average size of the particles is less than about 500 nm. In one embodiment, the average size of the particles is less than about 400 nm. In one embodiment, the average size of the particles is less than about 300 nm. In one embodiment, the average size of the particles is less than about 200 nm. In one embodiment, the average size of the particles is less than about 190 nm. In one embodiment, the average size of the particles is less than about 180 nm. In one embodiment, the average size of the particles is less than about 170 nm. In one embodiment, the average size of the particles is less than about 160 nm. In one embodiment, the average size of the particles is less than about 150 nm. In one embodiment, the average size of the particles is less than about 140 nm. In one embodiment, the average size of the particles is less than about 130 nm. In one embodiment, the average size of the particles is less than about 120 nm. In one embodiment, the average size of the particles is less than about 110 nm. In one embodiment, the average size of the particles is less than about 100 nm. In one embodiment, the average size of the particles is less than about 90 nm. In one embodiment, the average size of the particles is less than about 80 nm. In one embodiment, the average size of the particles is less than about 70 nm. In one embodiment, the average size of the particles is less than about 60 nm. In one embodiment, the average size of the particles is less than about 50 nm. In one embodiment, the average size of the particles is less than about 40 nm. In one embodiment, the average size of the particles is less than about 30 nm. In one embodiment, the average size of the particles is less than about 20 nm. In one embodiment, the average size of the particles is less than about 10 nm. In one embodiment, the average size of the particles is less than about 5 nm.

In one aspect, the compounds of the invention are formulated as particles further comprising a metal. In one embodiment, the metal is gold. In one embodiment, the metal is zirconium. In one aspect, the compounds of the invention are formulated as particles further comprising a metal oxide. In one embodiment, the metal oxide is iron oxide.

In another aspect, the compounds of the invention are formulated into compositions comprising an excipient. In one embodiment, the excipient is generally recognized as safe (GRAS). In one embodiment, the excipient is a surfactant. In one embodiment, the excipient is selected from the group consisting of Pluronic® F-68, Pluronic® F-108, KoVidone™ K17PF polyvinylpyrrolidone, sodium deoxycholate, and mannitol. Suitable surface modifiers can be selected from known organic and inorganic pharmaceutical excipients such as various polymers, low molecular weight oligomers, natural products and surfactants. Preferred surface modifiers include nonionic and anionic surfactants. Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986. Particularly preferred surface modifiers include polyvinylpyrrolidone, tyloxapol, poloxamers such as Pluronic™ F68 and F108, which are block copolymers of ethylene oxide and propylene oxide, and poloxamines such as Tetronic '908 (also known as Poloxamine 908), which is a tetrafunctional block copolymer derived from sequential addition of propylene oxide and ethylene oxide to ethylenediamine, available from BASF, dextran, lecithin, dialkylesters of sodium sulfosuccinic acid, such as Aerosol OTTM, which is a dioctyl ester of sodium sulfosuccinic acid, available from American Cyanamid, Duponol P, which is a sodium lauryl sulfate, available from DuPont, Triton™ X-200, which is an alkyl aryl polyether sulfonate, available from Rohm and Haas, Tween 80, which is a polyoxyethylene sorbitan fatty acid ester, available from ICI Specialty Chemicals, and Carbowax 3350 and 934, which are polyethylene glycols available from Union Carbide. Surface modifiers which have been found to be particularly useful include Tetronic 908, the Tweens, Pluronic F-68 and polyvinylpyrrolidone. Other useful surface modifiers include: decanoyl-N-methylglucamide; n-decyl j3-D-glucopyranoside; n-decyl j3-D-maltopyranoside; n-dodecyl j3-D-glucopyranoside; n-dodecyl j3-D-maltoside; heptanoyl-N-methylglucamide n-heptyl j3-D-glucopyranoside; n-heptyl j3-D-thioglucoside; n-hexyl j3-D-glucopyranoside; nonanoyl-N-methylglucamide; n-nonyl j3-D-glucopyranoside; octanoyl-N-methylglucamide; n-octyl j3-D-glucopyranoside; octyl j3-D-thioglucopyranoside; and the like.

In another aspect, the compounds of the invention are formulated into compositions comprising a polymeric resin. In general, polymeric resins suitable for use herein are chemically and physically inert, substantially free of metals, solvent and monomers, and of sufficient hardness and friability to enable them to avoid being chipped or crushed during grinding. Suitable polymeric resins include cross-linked polystyrenes, such as polystyrene crosslinked with divinylbenzene, styrene copolymers, polyacrylates such as polymethyl methacrylate, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacrylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body. The polymeric resin can have a density from 0.8 to 3.0 g/cm3. Higher density resins are preferred inasmuch as it is believed that these provide more efficient particle size reduction.

Prodrugs

The invention includes prodrugs of the compounds of the invention. "Prodrug," as used herein, means a compound which is convertible in vivo by metabolic means (e.g., by hydrolysis) to a compound of the present invention. Various forms of prodrugs are known in the art, for example, as discussed in Bundgaard, (ed.), Design of Prodrugs, Elsevier (1985); Widder et al. (ed.), Methods in Enzymology, vol. 4, Academic Press (1985); Krogsgaard-Larsen et al. (ed). "Design and Application of Prodrugs," Textbook of Drug Design and Development, Chapter 5, 113-191 (1991), Bundgaard et al., 1992, J. Drug Deliv. Rev. 8:1-38, Bundgaard, 1988, J. Pharm. Sci. 77:285 et seq.; and Higuchi and Stella (eds.), Prodrugs as Novel Drug Delivery Systems, American Chemical Society (1975). In one non-limiting example, the esters and amides of the alpha-carboxylic acid are prepared as prodrugs to improve oral bioavailability, whereby the ester or amide is stable in the stomach and gastrointestinal tract, is optimally transported across the lining of the gastrointestinal tract into the bloodstream, and is then converted by the ubiquitous esterases or amidases in the blood to the carboxylic acid moiety. In another non-limiting example, the ester prodrug is the methyl, ethyl, n-propyl or i-propyl ester. In another non-limiting example, the amide prodrug is the isopropyl amide or the 2,2,2-trifluoroethyl amide.

Salts

The compounds useful in the invention may form salts with acids or bases, and such salts are included in the present invention. In one embodiment, the salts are pharmaceutically-acceptable salts. The term "salts" embraces addition salts of free acids or free bases that are compounds useful within the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds useful in the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Methods of the Invention

In one aspect, the invention provides compounds useful to formulate a contrast composition for medical imaging, such as for example described in U.S. Pat. No. 5,451,393, description incorporated herein in its entirety.

In one aspect, the invention provides compounds capable of entering macrophages. In one embodiment, the mechanism of action is similar to that of a compound described by Hyafil et al., 2007, Nature Medicine, 13(5):636-641, description incorporated herein in its entirety. In another embodiment, the compound of the invention enters macrophages and modulates mTor. In another embodiment, the compound of the invention enters macrophages and inhibits mTor. In another embodiment, the compound of the invention enters macrophages and inhibits mTor, and acts as an imaging agent.

In one embodiment, the invention provides a method of treating one or more diseases or disorders associated with macrophages. In another embodiment, the invention provides a method of treating one or more diseases or disorders associated with mTor. In another embodiment, the invention provides a method of treating mTor- and macrophage-associated diseases and disorders. In another embodiment, the invention provides a method of treating mTor-associated diseases and disorders, by administering to a patient a therapeutically effective amount of a compound of the invention, or pharmaceutically acceptable salt of the same.

In one embodiment, the invention provides the use of the compounds of the invention, or pharmaceutically acceptable salts thereof, for the manufacture and preparation of medicaments for use in therapy. In another embodiment, a compound capable of entering macrophages retains its capability when mixed with an acceptable pharmaceutical carrier. In another embodiment, an effective inhibitor of mTor retains its activity when mixed with an acceptable pharmaceutical carrier. In another embodiment, the invention further provides novel compounds and novel pharmaceutical compositions comprising the same and at least one pharmaceutically acceptable carrier.

In one aspect, the invention provides compounds useful as theragnostics, or theranostics. Theragnostics, or theranostics, are compounds, formulations and compositions, capable of functioning as both therapeutic agents and diagnostic agents. For example, a compound of the invention can enter macrophages and modulate the activity of mTor in the macrophages, and at the same time provide for the possibility of imaging the macrophages distribution in the body. Modern approaches to theragnostics, or theranostics, have been described by Xie et al., 2010, Adv Drug Deliv Rev, 62(11):1064-1079, and Pene et al., 2009, Crit Care Med., 37(1 Suppl):S50-8, descriptions incorporated herein in their entirety.

Synthesis of the Compounds

The compounds of the invention can be prepared by a person skilled in the art of synthetic organic chemistry once armed with the teachings herein. The person skilled in the art knows how to select and implement appropriate synthetic routes. Suitable synthetic methods may be identifie206143d by reference to the literature describing synthesis of analogous compounds, and then performing the synthesis of the desired compound following the route used for the analogous compounds, modifying the starting materials, reagents, and reaction conditions as appropriate to synthesizing any particular desired compounds. In addition, reference may be made to sources such as Comprehensive Organic Synthesis, Ed. B. M. Trost and I. Fleming (Pergamon Press 1991), Comprehensive Organic Functional Group Transformations, Ed. A. R. Katritzky, O. Meth Cohn, and C. W. Rees (Pergamon Press, 1996), Comprehensive Organic Functional Group Transformations II, Ed. A. R. Katritzky and R. J. K. Taylor (Editor) (Elsevier, 2nd Edition, 2004), Comprehensive Heterocyclic Chemistry, Ed. A. R. Katritzky and C. W. Rees (Pergamon Press, 1984), and Comprehensive Heterocyclic Chemistry II, Ed. A. R. Katritzky, C. W. Rees, and E. F. V. Scriven (Pergamon Press, 1996), the entire disclosures of which are incorporated herein by reference.

In one embodiment of the invention, the starting materials and intermediates required for the synthesis may be obtained from commercial sources or synthesized according to methods known to those skilled in the art.

In a non-limiting embodiment, the synthesis of the compound of the invention is accomplished by the coupling an alcohol with a linker, and then with the alkaline salt of a carboxylic acid. In one embodiment, the first step is the reaction between a secondary alcohol and a bromo-substituted acyl chloride, resulting in an intermediate bromo-substituted ester. In one embodiment, the second step is the reaction between the intermediate bromo-substituted ester and the sodium salt of a carboxylic acid, resulting in a second ester.

In one embodiment, the synthetic scheme in Scheme 1 can be used.

Scheme 1
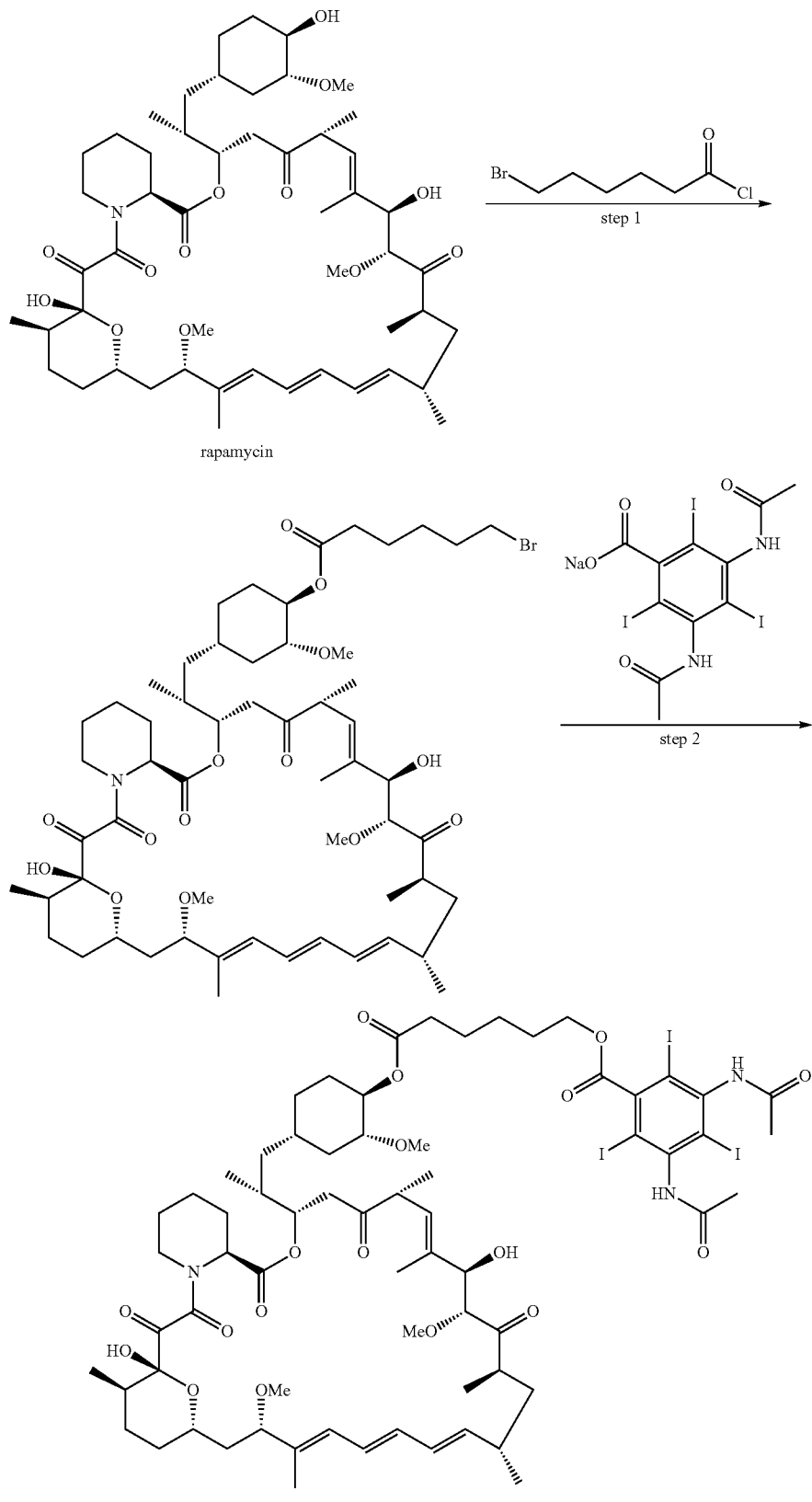

It will be understood that when compounds of the invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention that are efficacious in inhibiting mTor. The isomers resulting from the presence of a chiral center comprise a pair of non-superimposable isomers that are called "enantiomers." Single enantiomers of a pure compound are optically active, i.e., they are capable of rotating the plane of plane polarized light. Enantiomers may be purified from racemic mixtures by well-known chiral separation techniques. According to one such method, a racemic mixture of a compound having the structure of Formula I or a chiral intermediate thereof, is separated into 99% wt % pure optical isomers by HPLC using a suitable chiral column, such as a member of the series of DAICEL® CHIRALPAK® family of columns (Daicel Chemical Industries, Ltd., Tokyo, Japan), operated according to the manufacturer's instructions. By "isolated optical isomer" it is understood a compound that has been substantially purified from the corresponding optical isomer(s) of the same formula. In some embodiments, the isolated isomer is at least about 80% pure by weight. In some embodiments, the isolated isomer is at least about 90% pure by weight. In some embodiments, the isolated isomer is at least about 98% pure by weight. In some embodiments, the isolated isomer is at least about 99% pure, by weight. Diastereoisomeric pairs may be resolved by known separation techniques including normal and reverse phase chromatography, and crystallization.

Methods of Treating or Preventing

The invention includes methods of treating and preventing a disease or disorder associated with macrophages in a subject in need thereof. The invention also includes methods for treating or preventing in a subject a disease or disorder associated with mTor, and in particular but not limited to, a disease or disorder associated with mTor in macrophages. In some embodiments, the invention is a method of inhibiting mTor in a macrophage. In other embodiments, the invention is a method of inhibiting mTor in a macrophage of a subject having a disease or disorder associated with macrophages. In one embodiment, the subject is a human. In various embodiments, the disease and disorders associated with macrophages that are treatable or preventable using the methods of the invention include, but are not limited to atherosclerosis, sarcoidosis, diseases in which inflammation occurs in the lymph nodes, lungs, liver, eyes, skin, or other tissues, chronic obstructive pulmonary disease, emphysema, heart failure, vasculitis, rheumatoid arthritis, osteoarthritis, peripheral artery disease, sepsis, sepsis in late-stage cancer patients, ischemia, phlebitis, colitis, celiac disease, chronic inflammatory bowel disease, Crohn's disease, chronic prostatitis, interstitial cystitis, angiogenesis associated with tumor formation, cervical cancer, cardiomyopathy, and rhinitis.

In one embodiment, the method relies on the compounds of the invention ability to enter into macrophages, similarly to the compound described by Hyafil et al., 2007, Nature Medicine, 13(5):636-641, description incorporated herein in its entirety.

In one embodiment, the method comprises administering to the subject a therapeutically effective amount of a compound of the invention. In one embodiment, the method of treatment comprises administering to the subject a therapeutically effective amount of a compound of Formula 1. In one embodiment, the method of treatment comprises administering to the subject a therapeutically effective amount of a compound of Formula 2. In one embodiment, the method of treatment comprises administering to the subject a therapeutically effective amount of a compound of Formula 2.

In one embodiment, the compound of the invention is administered in combination with a second therapeutic agent for the treatment of a disease or disorder. In another embodiment, the second therapeutic agent is administered simultaneously, prior to, or after administration of the compound of the invention. In yet another embodiment, the second therapeutic agent is co-administered with the compound of the invention. In yet another embodiment, the second therapeutic agent is co-administered and co-formulated with the compound of the invention.

In one embodiment, the invention includes a method of preventing or treating a disease or disorder, comprising administering a compound of the invention to a subject in need of such prevention or treatment, wherein the amount of the compound is sufficient for the prevention or treatment of the disease or disorder in the subject.

Without wishing to be bound by any particular theory, it is believed that the ability of the compounds of the invention to enter macrophages provides methods of treating macrophages related disorders, and in particular, but not limited to, mTor and macrophages related disorders.

Also without wishing to be bound by any particular theory, it is believed that the ability of the compounds of the invention to regulate the biological activity of mTor, and in particular the biological activity of mTor in macrophages, provides methods of treating mTor related disorders, and in particular mTor and macrophages related disorders. For example, the compounds of the invention can be used to suppress, inhibit, or modulate mTor activity, and in particular mTor activity in macrophages, whether mTor is overexpressed or not.

Dosing

The compounds of the invention, alone or in combination with another therapeutic agent, can be administered to a cell, a tissue, or a subject to provide a therapeutic effect. Methods for the safe and effective administration of the compounds of the invention are known to those skilled in the art. For instance, the administration of mTor inhibitors is described in the literature.

Dosages of the compounds of the invention range from about 0.1 g/day to 10,000 mg/day, from about 1 µg/day to 1000 mg/day, and from about 10 g/day to 100 mg/day, and any and all whole or partial increments there between.

Stated in terms of subject body weight, dosages range from about 0.1 g/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

Oral dosages of the compounds of the invention range from about 0.1 µg/day to about 10,000 mg/day, from about 1 µg/day to about 1000 mg/day, from about 10 µg/day to about 100 mg/day, and from about 8 mg/day to about 80 mg/day, and any and all whole or partial increments there between.

Stated in terms of subject body weight, oral dosages range from about 0.1 µg/kg/day to about 1000 mg/kg/day, from about 10 µg/kg/day to about 500 mg/kg/day, from about 20 µg/kg/day to about 100 mg/kg/day, from about 50 µg/kg/day to about 50 mg/kg/day, and from about 0.10 mg/kg/day to about 5 mg/kg/day, and any and all whole or partial increments there between.

The compounds of the invention for administration can be administered in a dose range of from about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, and any and all whole or partial increments there between.

In some embodiments, the dose of the compound of the invention is from about 0.0001 mg to about 25 mg. In some embodiments, a dose of a compound of the invention used in compositions described herein is less than about 100 mg, or less than about 80 mg, or less than about 60 mg, or less than about 50 mg, or less than about 30 mg, or less than about 20 mg, or less than about 10 mg, or less than about 5 mg, or less than about 2 mg, or less than about 0.5 mg. Similarly, in some embodiments, a dose of a second compound as described herein is less than about 1000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments there between.

Pharmaceutical Composition

For administration of a compound of the present invention to a subject, the compound can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein.

The pharmaceutical compositions comprising a compound of the invention may be prepared, packaged, or sold in the form of a sterile injectable aqueous or oily suspension or solution. This suspension or solution may be formulated according to the known art, and may comprise, in addition to the active ingredient, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The compositions of the invention are preferably administered to the subject as a pharmaceutical or veterinary composition, which includes systemic and topical formulations. Among these, preferred are formulations suitable for inhalation, or for respirable, buccal, oral, rectal, vaginal, nasal, intrapulmonary, ophthalmic, optical, intracavitary, intratracheal, intraorgan, topical (including buccal, sublingual, dermal and intraocular), parenteral (including subcutaneous, intradermal, intramuscular, intravenous and intraarticular) and transdermal administration, among others. The route(s) of administration will be readily apparent to the skilled artisan and will depend upon any number of factors including the type and severity of the disease being treated, the type and age of the veterinary or human patient being treated.

The compositions of the invention may be administered to the lungs of a subject by any suitable means, but are preferably administered by generating an aerosol or spray comprised of respirable, inhalable, nasal or intrapulmonarily delivered particles comprising the active compound, which particles the subject inhales, i.e., by inhalation administration. The respirable particles may be liquid or solid. Particles comprising the active compound for practicing the present invention should include particles of respirable or inhalable size; that is, particles of a size sufficiently small to pass through the mouth and larynx upon inhalation and into the bronchi and alveoli of the lungs. In general, particles ranging from about 0.05, about 0.1, about 0.5, about 1, about 1.5 to about 5, about 6, about 7, about 8, about 10 microns in size, more particularly particles about 0.5 to less than about 5 microns in size, are respirable or inhalable. When particles of nonrespirable size are included in the aerosol or spray, they tend to deposit in the throat and be swallowed. Thus, the quantity of non-respirable particles in the aerosol or spray is preferably minimized when intended for respirable administration or by inhalation. For nasal or intrapulmonary administration, a particle size in the range of about 10, about 11, about 15, about 20 to about 25, about 30, about 40, about 50, and sometimes even up to about 100 and about 500 microns is preferred to ensure retention in the nasal or pulmonary cavity. Pulmonary instillation is particularly useful in treating newborns.

Liquid pharmaceutical compositions of the compound of the invention for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio, e.g., a 1 to 1 ratio by weight. Other therapeutic and formulation compounds may also be included, such as a surfactant to improve the state of surfactant in the lung and to help with the absorption of the active agent.

Aerosols of liquid particles comprising the active compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer consist of the active ingredient in liquid carrier, the active ingredient comprising up to 40% w/w of the compositions, but preferably less than 20% w/w, and the carrier is typically water or a dilute aqueous alcoholic solution, preferably made isotonic with body fluids by the addition of, for example sodium chloride. Optional additives include preservatives if the composition is not prepared sterile, for example, methyl hydroxybenzoate, antioxidants, flavoring agents, volatile oils, buffering agents and surfactants.

Aerosols of solid particles comprising the active compound may likewise be produced with any sold particulate medicament aerosol generator. Aerosol generators for administering solid particulate medicaments to a subject produce particles which are respirable, as explained above, and they generate a volume of aerosol containing a predetermined metered dose of a medicament at a rate suitable for human administration. Examples of such aerosol generators include metered dose inhalers and insufflators.

Pharmaceutical compositions that are useful in the methods of the invention may be administered systemically in oral solid formulations, ophthalmic, suppository, aerosol, topical or other similar formulations. In addition to the compounds of the invention, or a biological equivalent thereof, such pharmaceutical compositions may contain pharmaceutically-acceptable carriers and other ingredients known to enhance and facilitate drug administration.

The pharmaceutical compositions described herein can be prepared alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In yet another embodiment, compositions of the invention may be administered to the desired location of a subject by a transdermal patch. A transdermal patch is meant a system capable of delivery of a compound to a subject via the skin, or any suitable external surface, including mucosal membranes, such as those found inside the mouth. Such delivery systems generally comprise a flexible backing, an adhesive and a compound retaining matrix, the backing protecting the adhesive and matrix and the adhesive holding the whole on the skin of the subject. On contact with the skin, the compound-retaining matrix delivers the compound to the skin, the compound then passing through the skin into the subject's system.

Certain embodiments of the invention provide a pharmaceutical preparation/dosage formulation provided in the form of a transdermal patch and formulated for sustained release formulation, in a therapeutically effective amount sufficient to treat a disease associated with activation of an immune cell (e.g., rheumatoid arthritis) in a patient, wherein the dosage formulation, when administered (provided as a patch) to the patient, provides a substantially sustained dose over at least about 2 hours, 4 hours, 6 hours, 8, hours, 12 hours, 20 hours, or at least about 24 hours.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

A pharmaceutical composition of the invention may be prepared, packaged, or sold in a formulation suitable for pulmonary administration via the buccal cavity. Such a formulation may comprise dry particles that comprise the active ingredient and that have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful in pulmonary delivery are also useful in intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, PA), which is incorporated herein by reference.

Typically, dosages of the compound of the invention which may be administered to a subject, preferably a human, will vary depending upon any number of factors, including but not limited to, the type of animal and type of disease state being treated, the age of the subject and the route of administration.

The compound can be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, and the like.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experiments disclosed herein were designed to generate novel conjugates capable of penetrating macrophages. The experiments disclosed herein were further designed to generate novel conjugates capable of modulating mTor, in particular, but not limited to, mTor in macrophages. The materials and methods employed in these experiments are now described.

Example 1: Synthesis

Unless otherwise stated, temperatures are given in degrees Celsius (° C.); operations were carried out at room or ambient temperature, "rt," or "RT," (typically in the range of 18-25° C.); evaporation of solvents was carried out using a rotary evaporator under reduced pressure (typically 4.5-30 mm Hg) with a bath temperature of up to 60° C.; the course of the reactions was typically followed by thin layer chromatography (TLC); melting points are uncorrected; products exhibited satisfactory $^1$H-NMR and/or microanalytical data; the following conventional abbreviations are used: L (liters), mL (milliliters), mmol (millimoles), g (grams), mg (milligrams), min (minutes), and h (hours).

Unless otherwise specified, all solvents and reagents were purchased from commercial suppliers and used without further purification. Reactions were conducted under a blanket of nitrogen unless otherwise stated. Compounds were visualized under UV lamp (254 nm). $H^1$ NMR and $C^{13}$ NMR spectra were recorded on a 300 MHz NMR instrument.

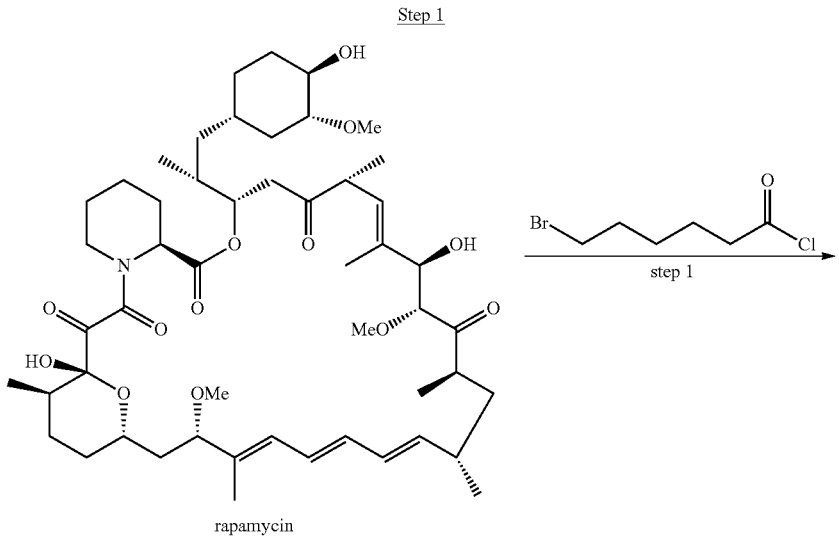

Step 1 rapamycin

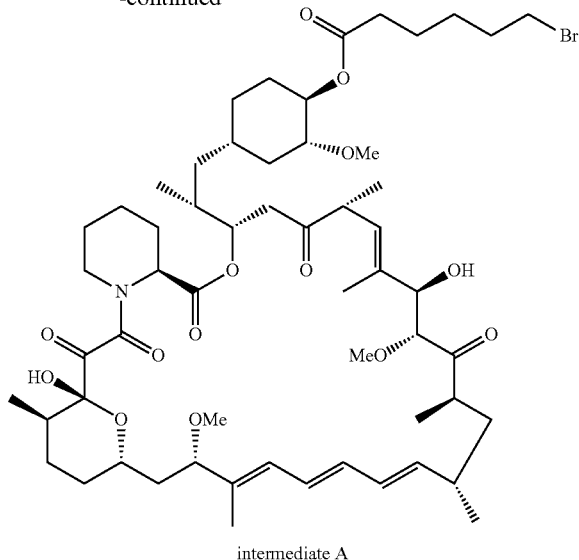

intermediate A

Figure 2:
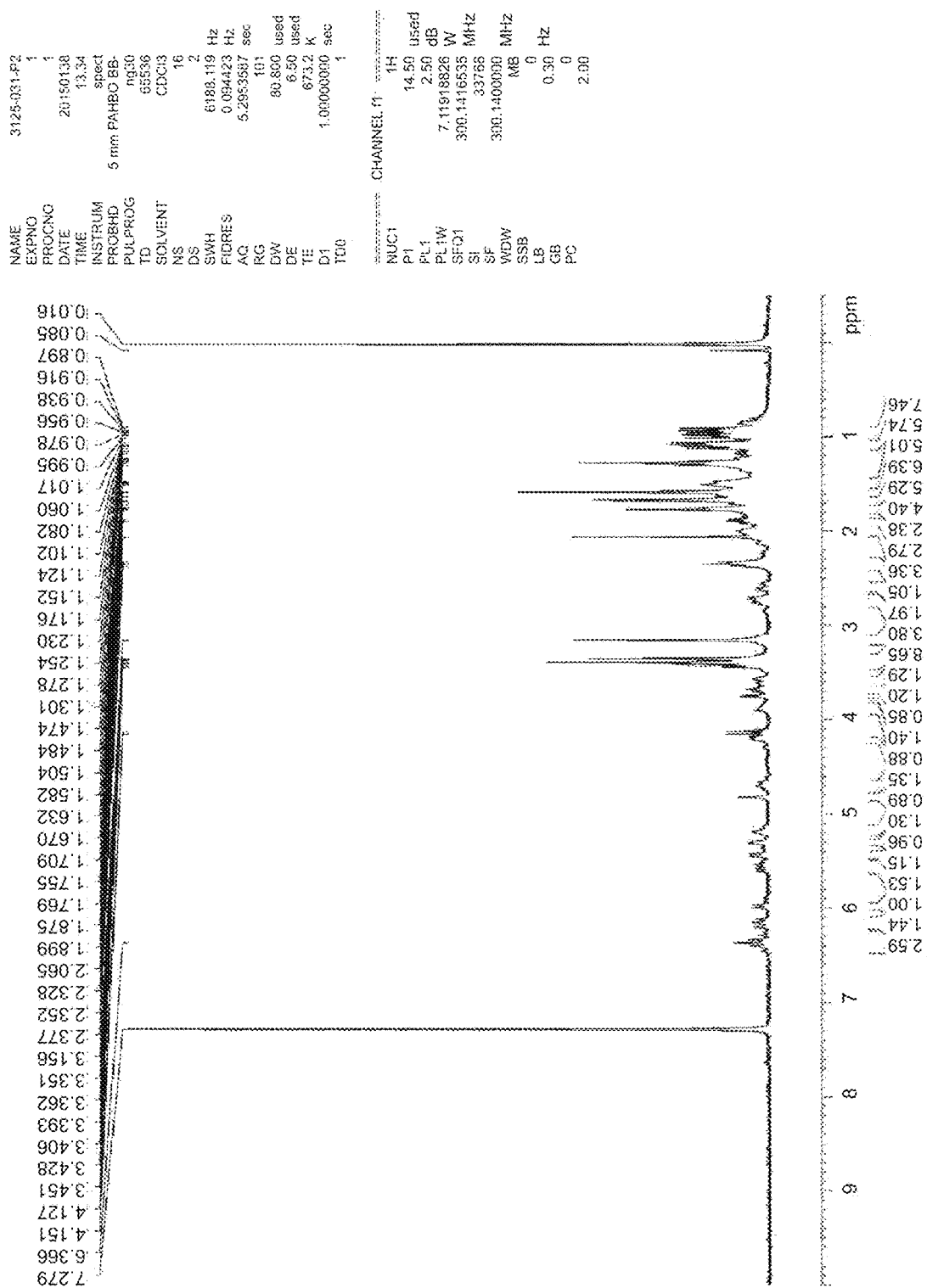
FIG. 2 depicts a $^1$H-NMR spectrum of intermediate A.

To a solution of rapamycin (200 mg, 0.22 mmol) and pyridine (174 mg, 2.2 mmol) in dry DCM (4 mL) was added a solution of 6-bromohexanoyl chloride (85 mg, 0.4 mmol) in dry DCM (1 mL) at −5° C. dropwise over a period of ~10 min under nitrogen. The reaction was stirred at RT for 2 hrs. TLC analysis indicated ~90% conversion of rapamycin. The reaction was quenched with water (3 mL). The reaction was combined with a previous batch (#3125-029) for work-up. The organic layer was separated and aqueous layer was extracted with ethyl acetate (3 mL×3). The organic layers were combined and washed with water (3 mL×2), 1N HCl (3 mL×2) and water (3 mL). After drying over anhydrous Na$_2$SO$_4$, filtration and solvent removal, the crude mixture containing intermediate A (~300 mg) was purified by silica gel column (eluent: hexane/ethyl acetate=3/1~2/1) to produce intermediate A (170 mg) as white foam. The yield was 57%. LCMS (ESI+): m/z 1114 (M+Na). The analytical data is depicted in FIG. 1 (mass spectrum of intermediate A), and FIG. 2 ($^1$H-NMR spectrum of intermediate A).

| Batch Summary of Step 1 | | | | |
|---|---|---|---|---|
| Batch # | rapamycin | intermediate A | Purity | Yield (%) |
| 3125-029 | 50 mg | 170 mg | TLC: OK | 57% |
| 3125-031 | 200 mg | (combined) | | |

Step 2

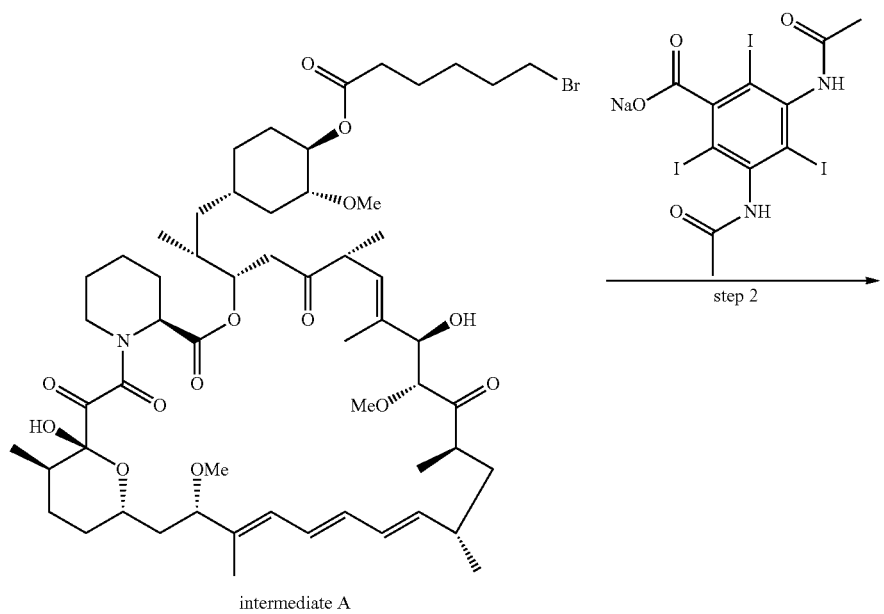

intermediate A

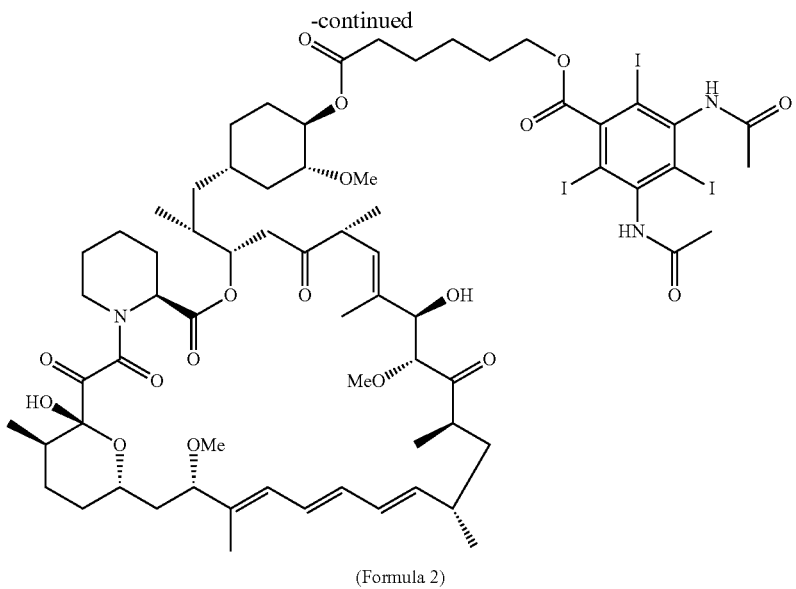

(Formula 2)

Figure 3:
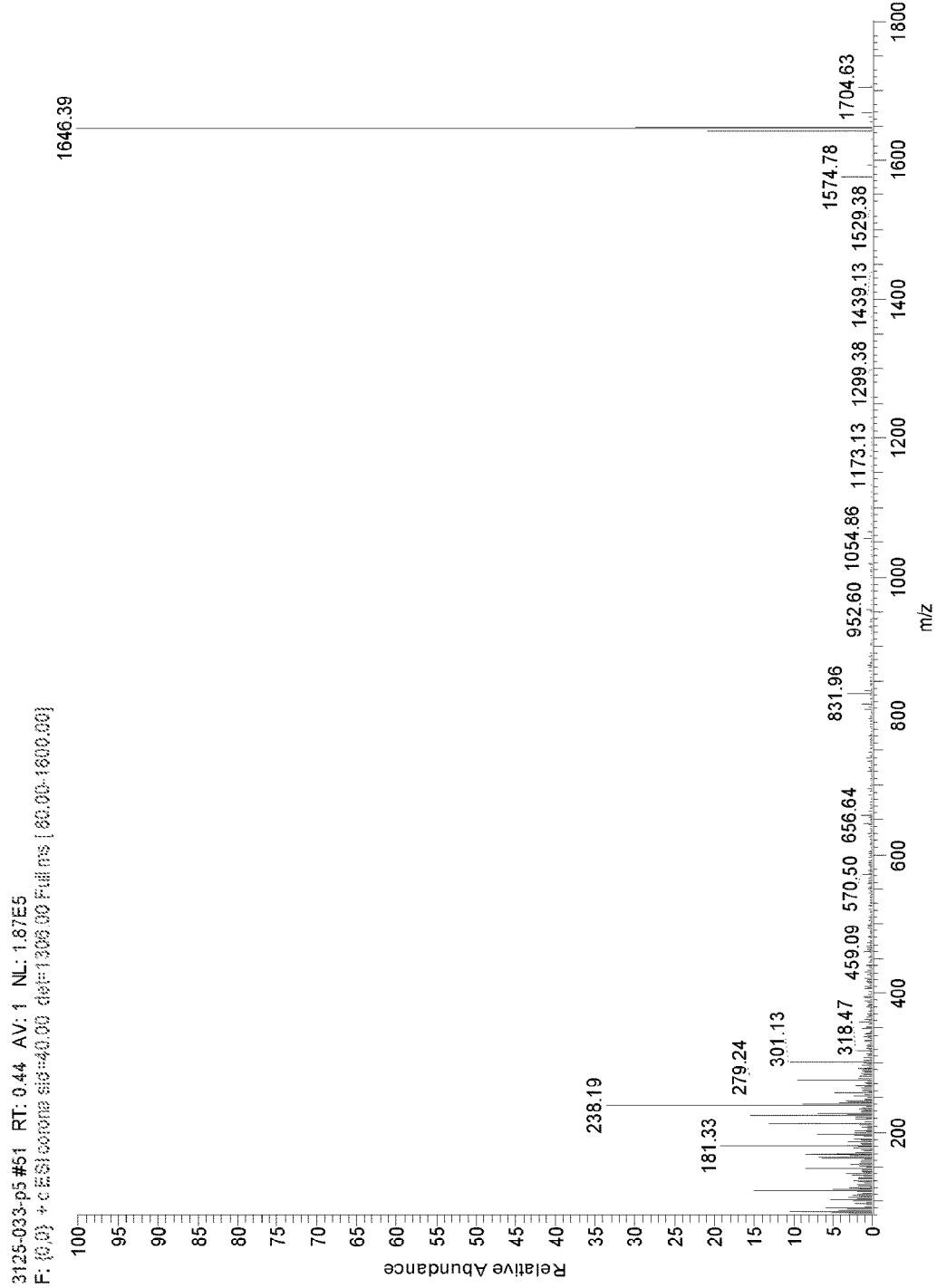
FIG. 3 depicts a mass spectrum of the compound represented by Formula 2.
Figure 4:
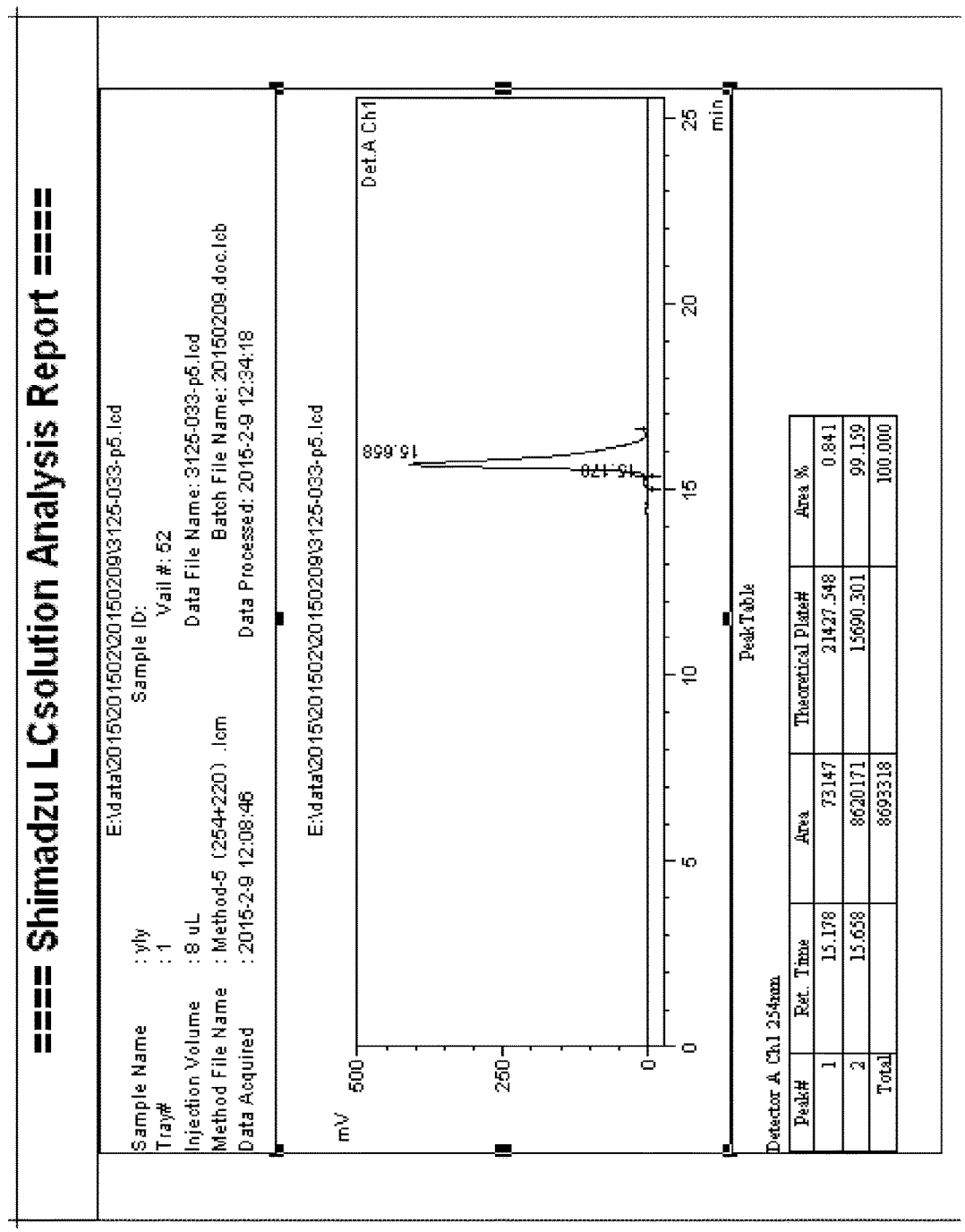
FIG. 4 depicts an HPLC chromatogram of the compound represented by Formula 2.
Figure 5:
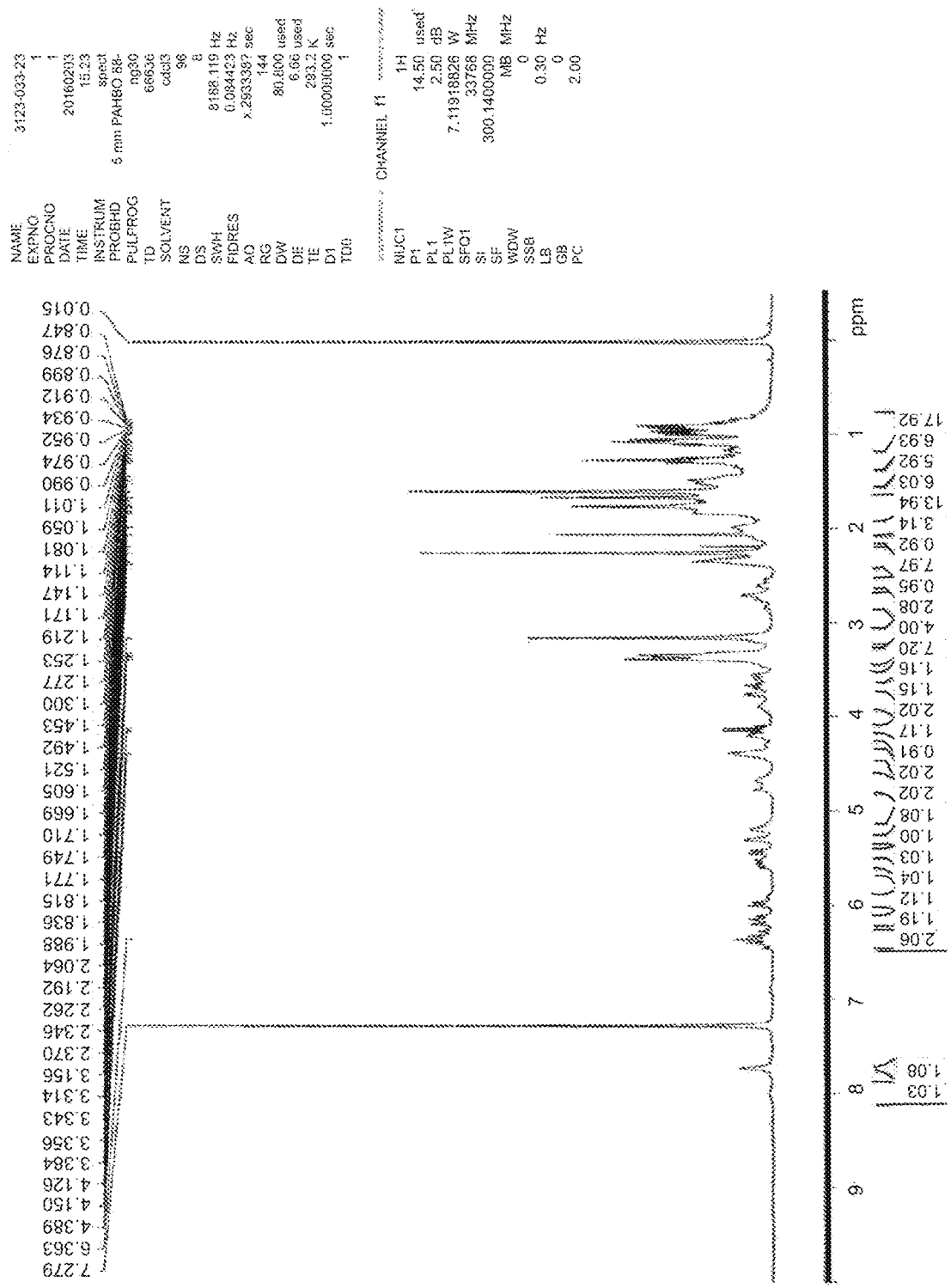
FIG. 5 depicts a $^1$H-NMR spectrum of the compound represented by Formula 2.

To a solution of sodium 3,5-diacetamido-2,4,6-triiodobenzoate (99 mg, 0.155 mmol) in DMF (2 mL) was added intermediate A (170 mg, 0.155 mmol) at RT in one portion. The reaction was stirred at RT overnight. After the conversion of intermediate A was ~70% as indicated by TLC, the reaction mixture was poured into icy-water (12 mL). After stirring for 30 min, the suspension was filtrated. The filter cake was washed with water (2 mL×4). The solid was dissolved in ethyl acetate, dried over anhydrous $Na_2SO_4$, filtrated and concentrated. 200 mg of crude Formula 2 product was obtained. Crude Formula 2 product was dissolved in ethyl acetate (1 mL) at RT. The EtOAc solution of the crude 2 was slowly added into a solution of hexane (2 mL) dropwise and stirred at RT for 30 min. The solid formed was collected by vacuum filtration. The filter cake was washed with hexane to provide 130 mg of Formula 2 product. TLC analysis showed that the product contained ~5% of intermediate A. Formula 2 product was further purified by recrystallization in ethyl acetate/hexane (0.75 mL/0.75 mL) to produce 95 mg of pure Formula 2 product as off-white solid. TLC showed a single spot. HPLC analysis showed 90% purity (Note 1). The 95 mg of Formula 2 product was further purified multiple times by silica gel column (70 mg, HPLC: 93%), by recrystallization in MTBE/ethyl acetate=3 mL/1 mL at 40° C. (35 mg, HPLC: 88%), and by preparative TLC (25 mg. HPLC: 99%, Note 2). 25 mg of Formula 2 product was combined with another batch of Formula 2 product (24 mg. 3125-037) to provide 48 mg of Formula 2 product as yellow solid. The yield was 10%. The analytical data is depicted in FIG. 3 (mass spectrum of the compound represented by Formula 2), FIG. 4 (HPLC chromatogram of the compound represented by Formula 2), and FIG. 5 ($^1$H-NMR spectrum of the compound represented by Formula 2).

LCMS (ESI+): m/z 1146 (M+Na); HPLC: 99.2%; H-NMR (300 MHz, CDCl3) δ 8.00 (brs, 1H), 7.75 (brs, 1H), 6.20-6.45 (m, 2H), 6.20-6.05 (m, 1H), 5.90-6.00 (m, 1H), 5.55-5.45 (m, 1H), 5.45-5.35 (m, 1H), 5.30-5.20 (m, 1H), 5.20-5.05 (m, 1H), 4.80-4.60 (m, 2H), 4.50-4.35 (m, 2H), 4.25-4.15 (m, 1H), 4.00-3.70 (m, 2H), 3.70-3.60 (m, 1H), 3.60-3.50 (m, 1H), 3.50-3.20 (m, 7H), 3.20-3.05 (m, 4H), 2.90-2.70 (m, 2H), 2.65-2.50 (m, 1H), 2.40-2.25 (m, 8H), 2.15-2.05 (m, 1H), 2.00-1.90 (m, 3H), 1.90-1.65 (m, 14H), 1.65-1.55 (m, 6H), 1.55-1.40 (m, 6H), 1.40-1.20 (m, 7H), 1.20-0.80 (m, 18H).

| Batch Summary of Step 2 | | | | |
|---|---|---|---|---|
| Batch # | Intermediate A | Formula 2 product | Purity | Yield (%) |
| 3125-033 | 170 mg | 25 mg | HPLC 99% | 10% |
| 3125-037 | 60 mg | 24 mg | | |

Notes
1. The HPLC purity may not be true. It was found that the compound of Formula 2 was not stable under some HPLC conditions. The HPLC purity is greatly dependent upon the HPLC mobile phases. With MeOH/$H_2O$/0.05% of TFA buffer, the HPLC purity is 90%. With MeOH/H₂O mobile phase, the HPLC purity is 91.7%. With acetonitrile/H₂O mobile phase, the HPLC purity is 99%. The same stability issues in HPLC mobile phases were also observed for rapamycin itself.

| Column | Agilent ZORBAX SB-C18 4.6*150 mm 0.35 um | | |
|---|---|---|---|
| Mobile phase | C: CAN D: H20 | | |
| | Time (mins) | % C | % D |
| Gradient | 0.01 | 10 | 90 |
| | 0.50 | 10 | 90 |
| | 8.00 | 90 | 10 |
| | 20.00 | 90 | 10 |
| | 20.10 | 10 | 90 |
| | 25.00 | 10 | 90 |
| | 25.10 | Stop | |
| Flow Rate | 0.8 ml/min | | |
| Temperature | Ambient | | |
| Run Time | 25.0 mins | | |
| Detection | 254&220 | | |

The disclosures of each and every patent, patent application, and publication cited herein are hereby incorporated herein by reference in their entirety. While the invention has been disclosed with reference to specific embodiments, it is apparent that other embodiments, and variations of this invention, may be devised by others skilled in the art without departing from the true spirit and scope of the invention. The appended claims are intended to be construed to include all such embodiments and equivalent variations.

What is claimed is:

1. A process for preparing a product, comprising the steps:

coupling a secondary alcohol at carbon position 43 of rapamycin with a bromo-substituted acyl chloride to obtain an intermediate A, wherein R is X-L-Br, intermediate A

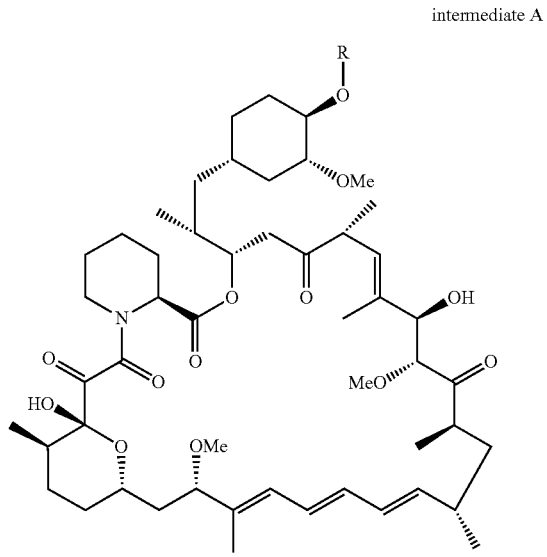

reacting intermediate A at room temperature in one portion to a solution of a sodium salt of a compound of Formula 1 in dimethylformamide:

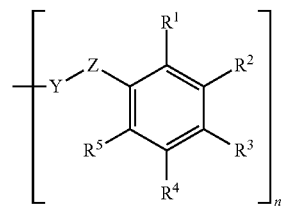

Formula 1 wherein,

X is carbonyl or a bond;

Y and Z are each independently selected from the group consisting of bond, oxygen, carbonyl, and amine, and Y having a point of attachment to L;

L is a linker comprising at least one selected from the group consisting of a bond, an alkyl, a branched alkyl, an aryl, an ester, an ether, and an amide;

$R^1$, $R^2$, $R^3$, $R^4$, and $R^5$ are each independently selected from the group consisting of H, F, Cl, Br, I, $NR^6R^7$, $NR^6C(=O)R^7$, $C_{1-6}$ alkyl, $C_{1-6}$ haloalkyl, $C_{2-6}$ alkenyl, $C_{2-6}$ alkynyl, wherein $R^6$ and $R^7$ are selected from the group consisting of H, and optionally substituted $C_{1-6}$ alkyl, $C_{1-6}$ haloalkyl, $C_{2-6}$ alkenyl, and $C_{2-6}$ alkynyl;

n is 1 or 2;

under reaction conditions effective to obtain a product of the formula

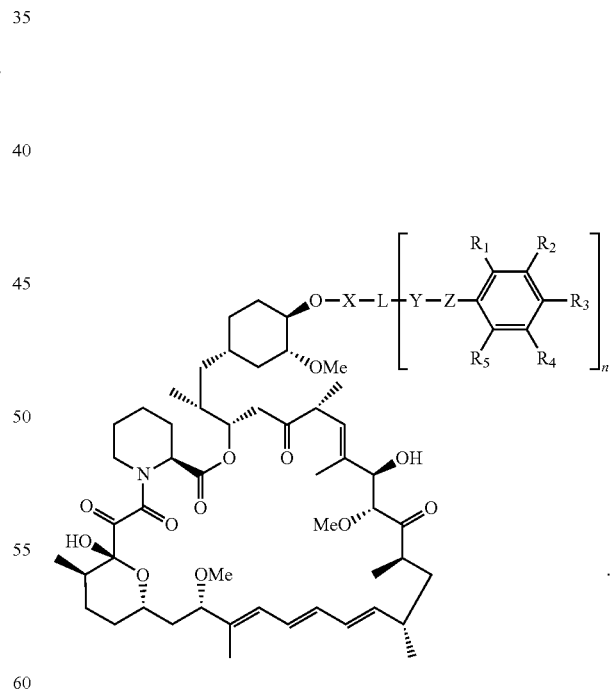

2. The process according to claim 1, wherein the product is selected from the group consisting of:

59
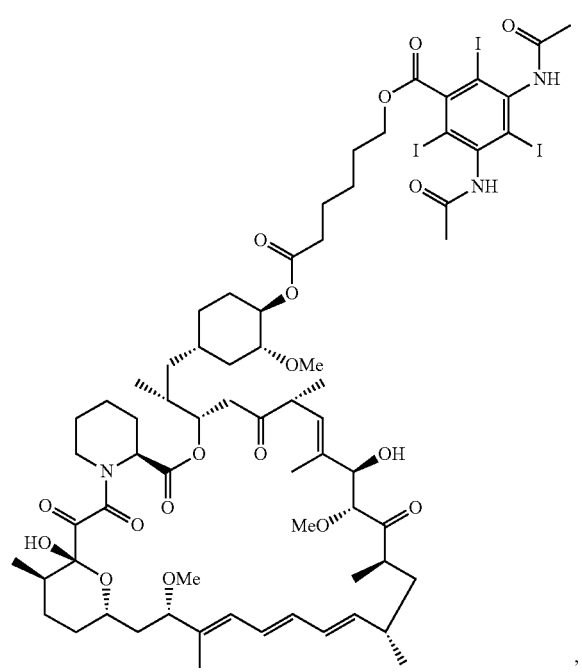 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)CCOCCOC(=O)c3c(I)c(NC(C)=O)c(I)c(NC(C)=O)c3I)[C@H](OC)C2)CC(=O)[C@H](C)/C=C(\C)[C@@H](O)[C@@H](OC)C(=O)[C@H](C)C[C@H](C)/C=C/C=C/C=C/1C]
,
60
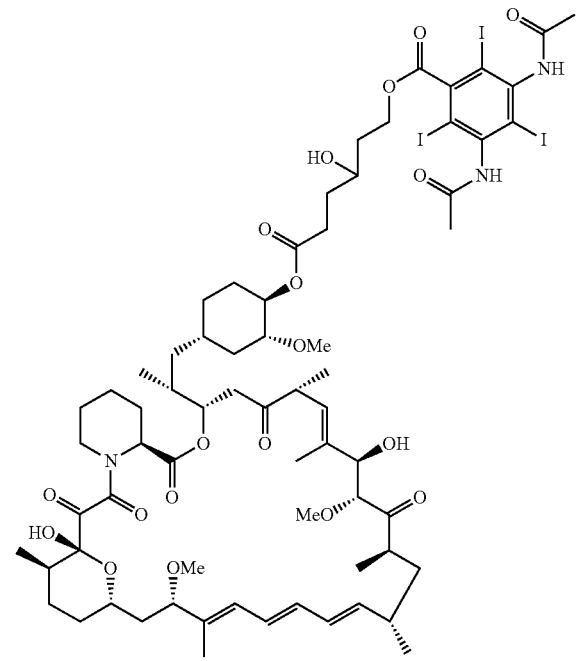
,
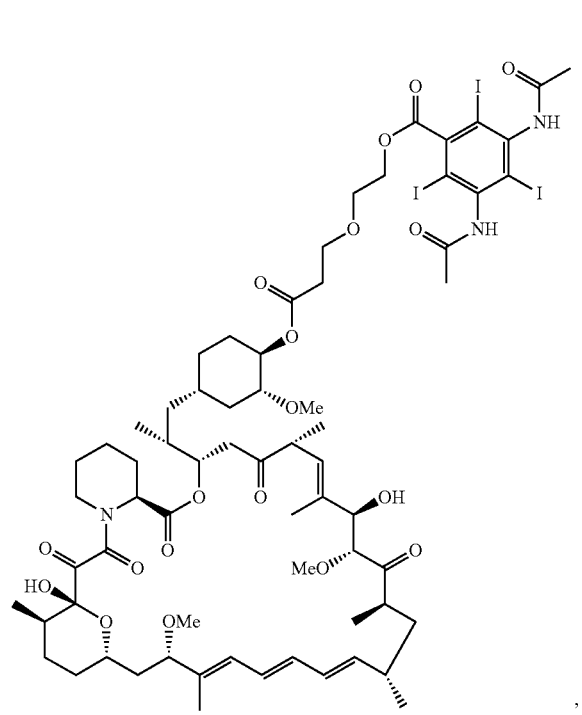
,
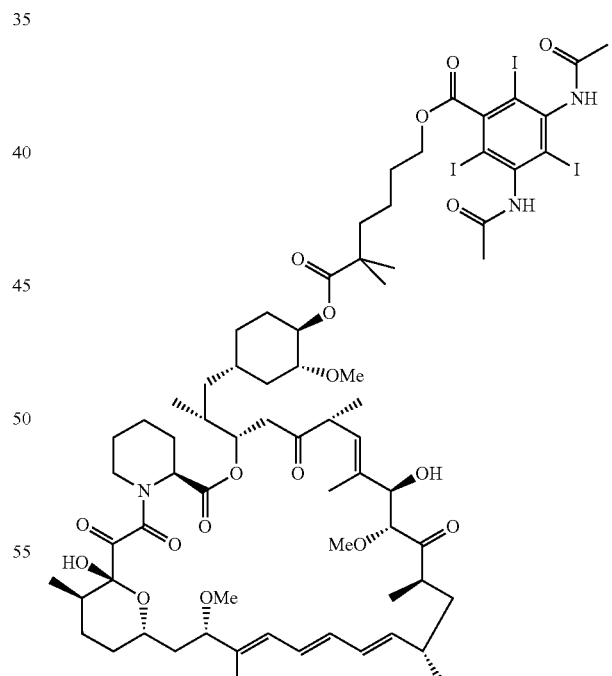
.
3. The process according to claim 1, wherein the product is represented by Formula 2:

Formula 2

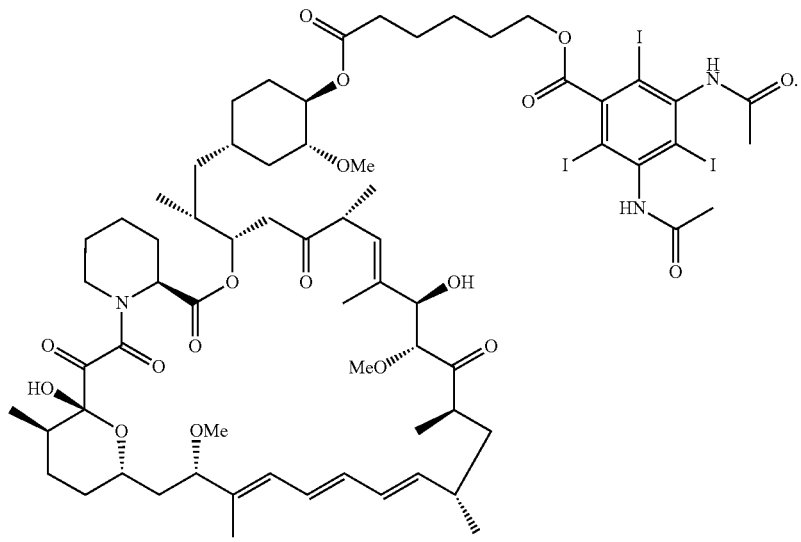

4. The process according to claim 1, further comprising the step of purifying the product by dissolving in ethyl acetate at room temperature, and then slowly adding ethyl acetate solution of the product into a solution of hexane dropwise and stirring at RT for 30 min, collecting a solid filter cake formed by vacuum filtration, and washing the filter cake with hexane.

5. The process according to claim 2, further comprising the step of purifying the product by recrystallization in ethyl acetate/hexane.

6. The process according to claim 1, wherein intermediate A is obtained by reacting a solution of rapamycin and pyridine in dry dichloromethane with a solution of 6-bromohexanoyl chloride in dry cold DCM under nitrogen under conditions effective to produce intermediate A.

\* \* \* \* \*